United States Patent
Matsumoto et al.

(10) Patent No.: US 9,566,218 B2
(45) Date of Patent: Feb. 14, 2017

(54) PRODUCTION METHOD OF COSMETIC, PREPARATION METHOD OF GEL FOR COSMETICS, AND METHOD OF REDUCING USE AMOUNT OF POLYMER THICKENER BLENDED IN COSMETIC RAW MATERIALS

(75) Inventors: Keigo Matsumoto, Funabashi (JP); Takayuki Imoto, Funabashi (JP); Takehisa Iwama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 332 days.

(21) Appl. No.: 14/008,912

(22) PCT Filed: Mar. 30, 2012

(86) PCT No.: PCT/JP2012/058610
§ 371 (c)(1),
(2), (4) Date: Dec. 11, 2013

(87) PCT Pub. No.: WO2012/133787
PCT Pub. Date: Oct. 4, 2012

(65) Prior Publication Data
US 2014/0113976 A1 Apr. 24, 2014

(30) Foreign Application Priority Data
Mar. 31, 2011 (JP) ................................ 2011-080670

(51) Int. Cl.
| | | |
|---|---|---|
| A61K 8/02 | (2006.01) | |
| A61K 8/04 | (2006.01) | |
| A61K 8/64 | (2006.01) | |
| A61Q 19/00 | (2006.01) | |
| A61K 8/73 | (2006.01) | |
| A61K 8/81 | (2006.01) | |

(52) U.S. Cl.
CPC ................ *A61K 8/042* (2013.01); *A61K 8/64* (2013.01); *A61K 8/73* (2013.01); *A61K 8/731* (2013.01); *A61K 8/8147* (2013.01); *A61Q 19/00* (2013.01); *A61K 2800/10* (2013.01); *A61K 2800/48* (2013.01); *A61K 2800/594* (2013.01)

(58) Field of Classification Search
CPC .......... A61K 8/64; A61K 8/731; A61K 8/042; A61K 8/73; A61K 8/8147; A61Q 19/00
See application file for complete search history.

(56) References Cited

U.S. PATENT DOCUMENTS

| | | |
|---|---|---|
| 2005/0142092 A1 | 6/2005 | Lintner |
| 2007/0048245 A1* | 3/2007 | Belfer ................ A61K 8/64 424/74 |
| 2007/0099842 A1* | 5/2007 | Ziegler ............... A61K 8/64 514/18.8 |
| 2008/0268127 A1 | 10/2008 | van de Velde |
| 2010/0279955 A1 | 11/2010 | Miyachi et al. |
| 2010/0291210 A1 | 11/2010 | Miyachi et al. |

FOREIGN PATENT DOCUMENTS

| | | |
|---|---|---|
| JP | A-2008-531011 | 8/2008 |
| WO | WO 2009/005151 A1 | 1/2009 |
| WO | WO 2009/005152 A1 | 1/2009 |
| WO | WO 2010/013555 A1 | 2/2010 |
| WO | WO 2010/106981 A1 | 9/2010 |
| WO | WO 2011/052613 A1 | 5/2011 |

OTHER PUBLICATIONS

Oct. 20, 2014 Extended Search Report issued in European Application 12 76 2840.2.
International Search Report issued in International Application No. PCT/JP2012/058610 mailed Jul. 3, 2012 (with translation).

* cited by examiner

*Primary Examiner* — Snigdha Maewall
(74) *Attorney, Agent, or Firm* — Oliff PLC

(57) ABSTRACT

There is provided a production method of a cosmetic, a preparation method of a gel for cosmetics, and a method of reducing the use amount of a polymer thickener blended in cosmetic raw materials. The present invention relates to a production method of a cosmetic comprising blending, into the cosmetic raw material in addition to the polymer thickener, at least one lipid peptide-type gelator that contains a low-molecular lipid peptide or a pharmaceutically usable salt thereof at a ratio of 0.1% by weight to 0.5% by weight based on a mass of the polymer thickener to form a thickening gel; a preparation method of a gel for cosmetics comprising blending, into an aqueous medium for cosmetics, a polymer thickener and at least one lipid peptide-type gelator that contains a low-molecular lipid peptide or a pharmaceutically usable salt thereof at the above-mentioned ratio to form a gel; and a method of reducing the use amount of a polymer thickener in production of a cosmetic comprising blending, into the cosmetic raw material in addition to the polymer thickener, at least one lipid peptide-type gelator that contains a low-molecular lipid peptide or a pharmaceutically usable salt thereof at the above-mentioned ratio.

17 Claims, 1 Drawing Sheet

PRODUCTION METHOD OF COSMETIC, PREPARATION METHOD OF GEL FOR COSMETICS, AND METHOD OF REDUCING USE AMOUNT OF POLYMER THICKENER BLENDED IN COSMETIC RAW MATERIALS

TECHNICAL FIELD

The present invention relates to a production method of a cosmetic, a preparation method of a gel for cosmetics, and a method of reducing the use amount of a polymer thickener blended in cosmetic raw materials.

BACKGROUND ART

Conventionally, various additives have been blended in cosmetics in order to impart various effects such as moisturizing, preserving, and thickening effects to the cosmetics. For example, polymer thickeners such as carboxyvinyl polymers are generally blended in cosmetics in order to impart the thickening effect to the cosmetics.

However, if the use amount of the polymer thickener blended in a cosmetic is too large, the viscosity of the cosmetic increases to make it difficult to allow the cosmetic to uniformly gel. Moreover, the polymer thickener causes crinkles or dripping of the cosmetic to make the feel in use of the cosmetic unpleasant.

SUMMARY OF THE INVENTION

Problem to be Solved by the Invention

Based on the foregoing, there is a demand for reducing the use amount of a polymer thickener blended in a cosmetic thereby to allow the cosmetic containing the polymer thickener to uniformly gel, and, in addition, for reducing crinkles and dripping of the cosmetic due to inclusion of the polymer thickener, and improving the feel in use of the cosmetic.

The present invention is made based on the above-noted circumstances. The problem to be solved by the invention is to provide a production method of a cosmetic in which the use amount of a polymer thickener is significantly reduced when compared with the conventional use amount of a polymer thickener blended in cosmetic raw materials.

The present invention also provides a preparation method of a gel for cosmetics in which the use amount of a polymer thickener is significantly reduced when compared with the conventional use amount of a polymer thickener blended in a gel for cosmetics.

The present invention further provides a method of reducing the use amount of a polymer thickener blended in cosmetic raw materials.

Means for Solving the Problem

The inventors of the present invention have carried out intensive studies and, as a result, have found that the use amount of a polymer thickener blended in cosmetic raw materials is reduced by blending, into cosmetic raw materials, a low-molecular-weight lipid peptide-type gelator at a certain ratio relative to the amount of a polymer thickener included therein to achieve a synergistic effect of the lipid peptide-type gelator and the polymer thickener. This finding has led to completion of the invention.

Specifically, as a first aspect, a production method of a cosmetic for producing a cosmetic in which a polymer thickener is blended in a cosmetic raw material is characterized by comprising blending, into the cosmetic raw material in addition to the polymer thickener, at least one lipid peptide-type gelator that contains a low-molecular weight lipid peptide or a pharmaceutically usable salt of the low-molecular weight lipid peptide at a ratio of 0.1% by weight to 0.5% by weight based on a mass of the polymer thickener to form a thickening gel.

As a second aspect, in the production method of a cosmetic according to the first aspect, the polymer thickener is carboxyvinyl polymer, carboxymethylcellulose, gellan gum, or xanthan gum.

As a third aspect, in the production method of a cosmetic according to the second aspect, relative to a concentration of the low-molecular weight lipid peptide, when the polymer thickener is carboxyvinyl polymer, a concentration of the carboxyvinyl polymer is 0.025% by weight to 0.05% by weight, when the polymer thickener is carboxymethylcellulose, a concentration of the carboxymethylcellulose is 0.05% by weight to 0.1% by weight, when the polymer thickener is gellan gum, a concentration of the gellan gum is 0.05% by weight to 0.1% by weight, and when the polymer thickener is xanthan gum, a concentration of the xanthan gum is 0.05% by weight to 0.1% by weight.

As a fourth aspect, in the production method of a cosmetic according to any one of the first to the third aspects, a molecular weight of the low-molecular weight lipid peptide is 1,000 or less.

As a fifth aspect, in the production method of a cosmetic according to any one of the first to fourth aspects, the low-molecular weight lipid peptide is of Formula (1):

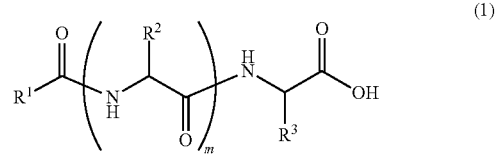

(where $R^1$ is a $C_{9-23}$ aliphatic group; $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH_2)$n-X group; at least one of $R^2$ and $R^3$ is a —$(CH_2)$n-X group; n is 1 to 4; X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms; and m is 1 to 3).

As a sixth aspect, in the production method of a cosmetic according to the fifth aspect, in Formula (1), $R^2$ is a hydrogen atom, a methyl group, an isopropyl group, an isobutyl group, or a sec-butyl group.

As a seventh aspect, in the production method of a cosmetic according to the fifth aspect, in Formula (1), $R^3$ is a 4-aminobutyl group, a 4-imidazole methyl group, a carbamoylmethyl group, a carbamoylethyl group, or a 3-methylindole group.

As an eighth aspect, in the production method of a cosmetic according to the fifth aspect, in Formula (1), $R^1$ is a $C_{13-17}$ aliphatic group, $R^2$ is a hydrogen atom, a methyl group, or an isopropyl group, and $R^3$ is a 4-aminobutyl group, a 4-imidazole methyl group, or a 3-methylindole group.

As a ninth aspect, in the production method of a cosmetic according to the eighth aspect, in Formula (1), $R^2$ is a hydrogen atom and $R^3$ is a 4-imidazole methyl group.

As a tenth aspect, a preparation method of a gel for cosmetics for preparing a thickening gel for cosmetics is characterized by comprising blending, into an aqueous medium for cosmetics, a polymer thickener and at least one lipid peptide-type gelator that contains a low-molecular weight lipid peptide or a pharmaceutically usable salt of the low-molecular weight lipid peptide at a ratio of 0.1% by weight to 0.5% by weight based on a mass of the polymer thickener to form a gel.

As an eleventh aspect, in the preparation method of a gel for cosmetics according to the tenth aspect, the polymer thickener is carboxyvinyl polymer carboxymethylcellulose, gellan gum, or xanthan gum.

As a twelfth aspect, in the preparation method of a gel for cosmetics according to the eleventh aspect, relative to a concentration of the low-molecular weight lipid peptide, when the polymer thickener is carboxyvinyl polymer, a concentration of the carboxyvinyl polymer is 0.025% by weight to 0.05% by weight, when the polymer thickener is carboxymethylcellulose, a concentration of the carboxymethylcellulose is 0.05% by weight to 0.1% by weight, when the polymer thickener is gellan gum, a concentration of the gellan gum is 0.05% by weight to 0.1% by weight, and when the polymer thickener is xanthan gum, a concentration of the xanthan gum is 0.05% by weight to 0.1% by weight.

As a thirteenth aspect, in the preparation method of a gel for cosmetics according to any one of the tenth to the twelfth aspects, a molecular weight of the low-molecular weight lipid peptide is 1,000 or less.

As a fourteenth aspect, in the preparation method of a gel for cosmetics according to any one of the tenth to the thirteenth aspects, the low-molecular weight lipid peptide is of Formula (I):

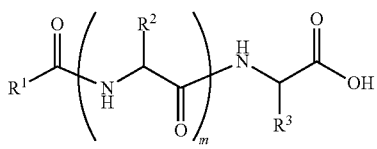

(1)

(where $R^1$ is a $C_{9-23}$ aliphatic group; $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH_2)n$-X group; at least one of $R^2$ and $R^3$ is a —$(CH_2)n$-X group; n is 1 to 4; X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring, and a 6-membered ring optionally containing 1 to 3 nitrogen atoms; and m is 1 to 3).

As a fifteenth aspect, in the preparation method of a gel for cosmetics according to the fourteenth aspect, in Formula (1), $R^2$ is a hydrogen atom, a methyl group, an isopropyl group, an isobutyl group, or a sec-butyl group.

As a sixteenth aspect, in the preparation method of a gel for cosmetics according to the fourteenth aspect, in Formula (1), $R^3$ is a 4-aminobutyl group, a 4-imidazole methyl group, a carbamoylmethyl group, a carbamoylethyl group, or a 3-methylindole group.

As a seventeenth aspect, in the preparation method of a gel for cosmetics according to the fourteenth aspect, in Formula (1), $R^1$ is a $C_{13-17}$ aliphatic group, $R^2$ is a hydrogen atom, a methyl group, or an isopropyl group, and $R^3$ is a 4-aminobutyl group, a 4-imidazole methyl group, or a 3-methylindole group.

As an eighteenth aspect, in the preparation method of a gel for cosmetics according to the seventeenth aspect, in Formula (1), $R^2$ is a hydrogen atom and $R^3$ is a 4-imidazole methyl group.

As a nineteenth aspect, a method of reducing the use amount of a polymer thickener in production of a cosmetic in which a polymer thickener is blended in a cosmetic raw material is characterized by comprising blending, into the cosmetic raw material in addition to the polymer thickener, at least one lipid peptide-type gelator that contains a low-molecular weight lipid peptide or a pharmaceutically usable salt of the low-molecular weight lipid peptide at a ratio of 0.1% by weight to 0.5% by weight based on a mass of the polymer thickener.

Effects of the Invention

In the production method of a cosmetic according to the present invention, a low-molecular-weight lipid peptide-type gelator is blended into cosmetic raw materials at a certain ratio relative to the amount of a polymer thickener included therein to achieve a synergistic effect of the lipid peptide-type gelator and the polymer thickener, which produces a cosmetic in which the use amount of the polymer thickener is significantly reduced when compared with the conventional use amount of a polymer thickener blended in cosmetic raw materials.

As a result, increase in viscosity of the cosmetic due to the polymer thickener can be suppressed, so that the cosmetic produced by the production method of a cosmetic according to the present invention can uniformly gel. In addition, crinkles and dripping of the cosmetic due to inclusion of the polymer thickener can be reduced, and the feel in use of the cosmetic can be improved.

In the preparation method of a gel for cosmetics according to the present invention, a low-molecular-weight lipid peptide-type gelator is blended into an aqueous medium at a certain ratio relative to the amount of a polymer thickener included therein to achieve a synergistic effect of the lipid peptide-type gelator and the polymer thickener, which makes it possible to prepare a gel for cosmetics in which the use amount of the polymer thickener is significantly reduced when compared with the conventional use amount of a polymer thickener blended in a gel for cosmetics. As a result, increase in viscosity of the cosmetic due to the polymer thickener can be suppressed, so that the gel for cosmetics prepared by the preparation method of a gel for cosmetics according to the present invention can be formed uniformly. In the cosmetic including the gel for cosmetics, crinkles or dripping of the cosmetic due to inclusion of the polymer thickener can be reduced, and the feel in use of the cosmetic can be improved.

In the method of reducing the use amount of a polymer thickener according to the present invention, a low-molecular-weight lipid peptide-type gelator is blended into cosmetic raw materials at a certain ratio relative to the amount of the polymer thickener included therein to achieve a synergistic effect of the lipid peptide-type gelator and the polymer thickener, which significantly reduces the use amount of the polymer thickener when compared with the conventional use amount of a polymer thickener blended in cosmetic raw materials.

MODES FOR CARRYING OUT THE INVENTION

[Lipid Peptide-Type Gelator]

Figure 1:
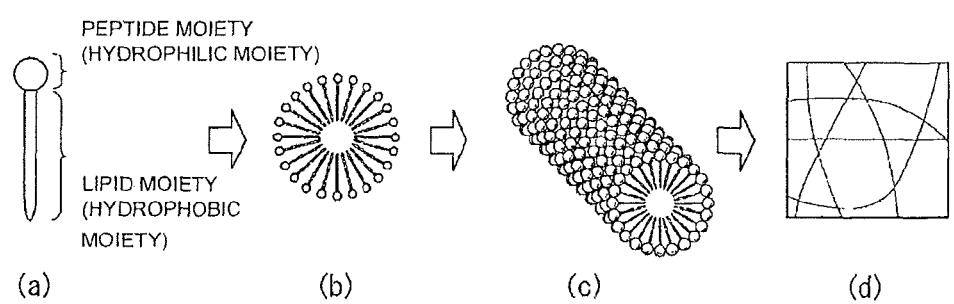
FIG. 1 is a conceptual view of self assembly and gelation of a lipid peptide-type gelator in a hydrophilic solution.

The present invention is characterized by blending at least one lipid peptide-type gelator that contains a low-molecular weight lipid peptide or a pharmaceutically usable salt thereof at a certain ratio to a polymer thickener.

Preferably, the molecular weight of the lipid peptide is 1,000 or less.

Examples of the low-molecular weight lipid peptide may include a lipid peptide that contains a lipid moiety and a peptide moiety of, for example, Formula (1).

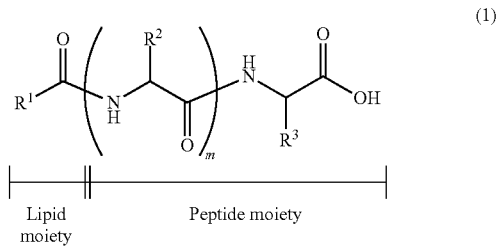

In Formula (1), $R^1$ is a $C_{9-23}$ aliphatic group and is preferably a $C_{13-17}$ aliphatic group.

Examples of the lipid moiety including $R^1$ and an adjacent carbonyl group may include a decoyl group, a dodecoyl group, an undecoyl group, a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, vaccenoyl group, an octadecylcarbonyl group, an arachidonoyl group, an icosanoyl group, a behenoyl group, an erucoyl group, a docosylcarbonyl group, a lignoceroyl group, and a nervonoyl group, and preferably include a myristoyl group, a tetradecylcarbonyl group, a palmitoyl group, a margaroyl group, an oleoyl group, an elaidoyl group, a linoleoyl group, a stearoyl group, and a vaccenoyl group.

In Formula (1), $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH_2)n$-X group, at least one of $R^2$ and $R^3$ is a —$(CH_2)n$-X group, n is 1 to 4, and X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms.

$R^2$ is preferably a hydrogen atom, a methyl group, an ethyl group, or a $C_{3-7}$ alkyl group that optionally contains a $C_{1-3}$ branched chain. Therefore, $R^2$ is preferably a hydrogen atom, a methyl group, an ethyl group, an n-propyl group, an isopropyl group, an n-butyl group, an isobutyl group, a sec-butyl group, a tert-butyl group, or the like, is further preferably a hydrogen atom, a methyl group, an isopropyl group, an isobutyl group, or a sec-butyl group, and is further more preferably a hydrogen atom.

$R^3$ is preferably a hydrogen atom, a methyl group, or a —$(CH_2)n$-X group, n is 1 to 4, and X is an amino group, a guanidino group, a —$CONH_2$ group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms.

In —$(CH_2)n$-X group as $R_3$, X is preferably an amino group, a guanidino group, a carbamoyl group, an imidazole group, a pyrazole group, or an indole group.

Therefore, —$(CH_2)n$-X group as $R_3$ is preferably an aminomethyl group, a 2-aminoethyl group, a 3-aminopropyl group, a 4-aminobutyl group, a carbamoylmethyl group, a 2-carbamoylethyl group, a 3-carbamoylpropyl group, a 2-guanidinoethyl group, a 3-guanidinopropyl group, a pyrrole methyl group, a 4-imidazole methyl group, a pyrazole methyl group, or a 3-indole methyl group, is more preferably a 4-aminobutyl group, a carbamoylmethyl group, a carbamoylethyl group, a 3-carbamoylpropyl group, a 4-imidazole methyl group, or a 3-indole methyl group, and is further more preferably a 4-imidazole methyl group.

In Formula (1), m that is the number of the repeating peptide structures is 1 to 3.

As for the compound of Formula (1), a lipid peptide that is particularly preferable as the lipid peptide-type gelator is the following compounds formed from a lipid moiety and an amino acid moiety or a peptide moiety. The abbreviations of amino acids are as follows: asparagine (Asn), alanine (Ala), glutamine (Gln), glycine (Gly), valine (Val), histidine (His), lysine (Lys), and leucine (Leu). Myristoyl-His, myristoyl-Lys, myristoyl-Asn, myristoyl-Gln, myristoyl-Gly-His, myristoyl-Gly-Lys, myristoyl-Gly-Asn, myristoyl-Gly-Gln, myristoyl-Gly-Gly-His, myristoyl-Gly-Gly-Lys, myristoyl-Gly-Gly-Asn, myristoyl-Gly-Gly-Gln, myristoyl-Gly-Gly-Gly-His, myristoyl-Gly-Gly-Gly-Lys, myristoyl-Gly-Gly-Gly-Asn, myristoyl-Gly-Gly-Gly-Gln, myristoyl-Gly-Gly-Gly-Gly-His, myristoyl-Gly-Gly-Gly-Gly-Lys, myristoyl-Lys, myristoyl-Asn, myristoyl-Gln, myristoyl-Ala-His, myristoyl-Ala-Lys, myristoyl-Ala-Asn, myristoyl-Ala-Gln, myristoyl-Ala-Ala-His, myristoyl-Ala-Ala-Lys, myristoyl-Ala-Ala-Asn, myristoyl-Ala-Ala-Gln, myristoyl-Ala-Ala-Ala-His, myristoyl-Ala-Ala-Ala-Lys, myristoyl-Ala-Ala-Ala-Asn, myristoyl-Ala-Ala-Ala-Gln, myristoyl-Ala-Ala-Ala-Ala-His, myristoyl-Ala-Ala-Ala-Ala-Lys, myristoyl-Ala-Ala-Ala-Ala-Asn, myristoyl-Ala-Ala-Ala-Ala-Gln, myristoyl-His, myristoyl-Lys, myristoyl-Asn, myristoyl-Gln, myristoyl-Val-His, myristoyl-Val-Lys, myristoyl-Val-Asn, myristoyl-Val-Gln, myristoyl-Val-Val-His, myristoyl-Val-Val-Lys, myristoyl-Val-Val-Asn, myristoyl-Val-Val-Gln, myristoyl-Val-Val-Val-His, myristoyl-Val-Val-Val-Lys, myristoyl-Val-Val-Val-Asn, myristoyl-Val-Val-Val-Gln, myristoyl-Val-Val-Val-Val-His, myristoyl-Val-Val-Val-Val-Lys, myristoyl-Val-Val-Val-Val-Asn, myristoyl-Val-Val-Val-Val-Gln, myristoyl-His, myristoyl-Lys, myristoyl-Asn, myristoyl-Gln, myristoyl-Leu-His, myristoyl-Leu-Lys, myristoyl-Leu-Asn, myristoyl-Leu-Gln, myristoyl-Leu-Leu-His, myristoyl-Leu-Leu-Lys, myristoyl-Leu-Leu-Asn, myristoyl-Leu-Leu-Gln, myristoyl-Leu-Leu-Leu-His, myristoyl-Leu-Leu-Leu-Lys, myristoyl-Leu-Leu-Leu-Asn, myristoyl-Leu-Leu-Leu-Gln, myristoyl-Leu-Leu-Leu-Leu-His, myristoyl-Leu-Leu-Leu-Leu-Lys, myristoyl-Leu-Leu-Leu-Leu-Asn, myristoyl-Leu-Leu-Leu-Leu-Gln; palmitoyl His, palmitoyl Lys, palmitoyl Asn, palmitoyl Gln, palmitoyl Gly-His, palmitoyl Gly-Lys, palmitoyl Gly-Asn, palmitoyl Gly-Gln, palmitoyl Gly-Gly-His, palmitoyl Gly-Gly-Lys, palmitoyl Gly-Gly-Asn, palmitoyl Gly-Gly-Gln, palmitoyl Gly-Gly-Gly-His, palmitoyl Gly-Gly-Gly-Lys, palmitoyl Gly-Gly-Gly-Asn, palmitoyl Gly-Gly-Gly-Gln, palmitoyl Gly-Gly-Gly-Gly-His, palmitoyl Gly-Gly-Gly-Gly-Lys, palmitoyl Gly-Gly-Gly-Gly-Asn, palmitoyl Gly-Gly-Gly-Gly-Gln, palmitoyl His, palmitoyl Lys, palmitoyl Asn, palmitoyl Gln, palmitoyl Ala-His, palmitoyl Ala-Lys, palmitoyl Ala-Asn, palmitoyl Ala-Gln, palmitoyl Ala-Ala-His, palmitoyl Ala-Ala-Lys, palmitoyl Ala-Ala-Asn, palmitoyl Ala-Ala-Gln, palmitoyl Ala-Ala-Ala-His, palmitoyl Ala-Ala-Ala-Lys, palmitoyl Ala-Ala-Ala-Asn, palmitoyl Ala-Ala-Ala-Gln, palmitoyl Ala-Ala-Ala-Ala-His, palmitoyl Ala-Ala-Ala-Ala-Lys, palmitoyl Ala-Ala-Ala-Ala-Asn, palmitoyl Ala-Ala-Ala-Ala-Gln, palmitoyl His, palmitoyl Lys, palmitoyl Asn, palmitoyl Gln, palmitoyl Val-His, palmitoyl Val-Lys, palmitoyl Val-Asn, palmitoyl Val-Gln, palmitoyl Val-Val-His, palmitoyl Val-Val-Lys, palmitoyl Val-Val-Asn, palmitoyl Val-Val-Gln, palmitoyl Val-Val-Val-His, palmitoyl Val-Val-Val-Lys, palmitoyl Val-Val-Val-Asn, palmitoyl Val-Val-Val-Gln, palmitoyl Val-Val-Val-Val-His, palmitoyl Val-Val-Val-Val-Lys, palmitoyl Val-Val-Val-Val-Asn, palmitoyl Val-Val-Val-Val-Gln, palmitoyl His, palmitoyl Lys, palmitoyl Asn, palmitoyl Gln, palmitoyl Leu-His, palmitoyl Leu-Lys, palmitoyl Leu-Asn, palmitoyl Leu-Gln, palmitoyl Leu-Leu-His, palmitoyl Leu-Leu-Lys, palmitoyl Leu-Leu-Asn, palmitoyl Leu-Leu-Gln, palmitoyl Leu-Leu-Leu-His, palmitoyl Leu-Leu-Leu-Lys, palmitoyl Leu-Leu-Leu-Asn, palmitoyl Leu-Leu-Leu-Gln, palmitoyl Leu-Leu-Leu-Leu-His, palmitoyl Leu-Leu-Leu-Leu-Lys, palmitoyl Leu-Leu-Leu-Leu-Asn, palmitoyl Leu-Leu-Leu-Leu-Gln; stearoyl His, stearoyl Lys, stearoyl Asn, stearoyl Gln, stearoyl Gly-His, stearoyl Gly-Lys, stearoyl Gly-Asn, stearoyl Gly-Gln, stearoyl Gly-Gly-His, stearoyl Gly-Gly-Lys, stearoyl Gly-Gly-Asn, stearoyl Gly-Gly-Gln, stearoyl Gly-Gly-Gly-His, stearoyl Gly-Gly-Gly-Lys, stearoyl Gly-Gly-Gly-Asn, stearoyl Gly-Gly-Gly-Gln, stearoyl Gly-Gly-Gly-Gly-His, stearoyl Gly-Gly-Gly-Gly-Lys, stearoyl Gly-Gly-Gly-Gly-Asn, stearoyl Gly-Gly-Gly-Gly-Gln, stearoyl His, stearoyl Lys, stearoyl Asn, stearoyl Gln, stearoyl Ala-His, stearoyl Ala-Lys, stearoyl Ala-Asn, stearoyl Ala-Gln, stearoyl Ala-Ala-His, stearoyl Ala-Ala-Lys, stearoyl Ala-Ala-Asn, stearoyl Ala-Ala-Gln, stearoyl Ala-Ala-Ala-His, stearoyl Ala-Ala-Ala-Lys, stearoyl Ala-Ala-Ala-Asn, stearoyl Ala-Ala-Ala-Gln, stearoyl Ala-Ala-Ala-Ala-His, stearoyl Ala-Ala-Ala-Ala-Lys, stearoyl Ala-Ala-Ala-Ala-Asn, stearoyl Ala-Ala-Ala-Ala-Gln, stearoyl His, stearoyl Lys, stearoyl Asn, stearoyl Gln, stearoyl Val-His, stearoyl Val-Lys, stearoyl Val-Asn, stearoyl Val-Gln, stearoyl Val-Val-His, stearoyl Val-Val-Lys, stearoyl Val-Val-Asn, stearoyl Val-Val-Gln, stearoyl Val-Val-Val-His, stearoyl Val-Val-Val-Lys, stearoyl Val-Val-Val-Asn, stearoyl Val-Val-Val-Gln, stearoyl Val-Val-Val-Val-His, stearoyl Val-Val-Val-Val-Lys, stearoyl Val-Val-Val-Val-Asn, stearoyl Val-Val-Val-Val-Gln, stearoyl His, stearoyl Lys, stearoyl Asn, stearoyl Gln, stearoyl Leu-His, stearoyl Leu-Lys, stearoyl Leu-Asn, stearoyl Leu-Gln, stearoyl Leu-Leu-His, stearoyl Leu-Leu-Lys, stearoyl Leu-Leu-Asn, stearoyl Leu-Leu-Gln, stearoyl Leu-Leu-Leu-His, stearoyl Leu-Leu-Leu-Lys, stearoyl Leu-Leu-Leu-Asn, stearoyl Leu-Leu-Leu-Gln, stearoyl Leu-Leu-Leu-Leu-His, stearoyl Leu-Leu-Leu-Leu-Lys, stearoyl Leu-Leu-Leu-Leu-Asn, and stearoyl Leu-Leu-Leu-Leu-Gln.

Most preferred examples thereof include myristoyl-His, myristoyl-Gly-His, myristoyl-Gly-Gly-His, myristoyl-Gly-Gly-Gly-His, myristoyl-Gly-Gly-Gly-Gly-His, palmitoyl-His, palmitoyl-Gly-His, palmitoyl-Gly-Gly-His, palmitoyl-Gly-Gly-Gly-His, palmitoyl-Gly-Gly-Gly-Gly-His, stearoyl-His, stearoyl-Gly-His, stearoyl-Gly-Gly-His, stearoyl-Gly-Gly-Gly-His, and stearoyl-Gly-Gly-Gly-Gly-His.

[Gel Formation Mechanism]

The gel formation mechanism of the lipid peptide-type gelator for use in the present invention is totally different from the mechanisms of formation of conventional polymer hydrogels. A low-molecular weight lipid peptide that is contained in the lipid peptide-type gelator self-assembles to form a fibrous configuration, and then the fibers form a network structure. The network structure encloses water, an alcohol, a polyhydric alcohol, a hydrophobic organic solvent, a hydrophilic organic solvent, or a miscible, mixed solution of these to form a gel.

When the lipid peptide-type gelator that contains the low-molecular weight lipid peptide of Formula (1) or a pharmacologically usable salt thereof is put into water or a hydrophilic solution such as hydrophilic mixed solutions, the peptide moieties in Formula (1) form an intermolecular non-covalent bond via a hydrogen bond, while the lipid moieties in Formula (1) self-assemble via hydrophobical packing, thereby a tubular secondary assembly, that is, a fiber is formed.

For reference, a conceptual view of self-assembly and gelation of a low-molecular weight lipid peptide in a hydrophilic solution is exemplified in FIG. 1 (however, not all the low-molecular weight lipid peptides in the present invention necessarily undergo the self-assembly or the gelation shown in FIG. 1). The low-molecular weight lipid peptides (a) assemble with each other (b) with their lipid moieties that are hydrophobic moieties arranged inside to form a fiber (c) via self-assembly.

As the lipid peptide-type gelator to be used in fiber formation, one of the lipid peptide-type gelators as described above may be used, or two or more thereof may be used in combination. Preferably, one or two thereof are used, and further preferably, one thereof is used. Using two or more of the lipid peptide-type gelators can be expected to obtain a characteristic different from the characteristic obtained when one thereof is used.

The fiber thus formed can adsorb or include a low-molecular weight compound. When the formed fiber includes the additives for use in cosmetics as described below such as hydrophobic compounds including vitamin E, such a fiber easily dissolves in an aqueous solution. As a result, both a hydrophilic compound such as vitamin C and a hydrophobic compound such as vitamin E can be dissolved in an aqueous solution. This also facilitates dissolution of a preservative that is less prone to dissolve in water, such as methylparaben. Therefore, in production of cosmetics, a hydrophobic organic solvent that is used to dissolve a hydrophobic compound can be partly replaced by water, a low-molecular weight alcohol, or a similar alternative, that is safer to the human bodies.

A gel that is formed with fibers including a low-molecular weight compound can have the so-called sustained release ability to gradually release the included low-molecular weight compound when applied on the skin or the hair. Therefore, the moisturizing effect and similar effects of cosmetics can be sustained.

The fiber that is formed in a hydrophilic solution forms a three-dimensional network structure (see (d) in FIG. 1, for example), and then a bond is formed between the peptide moiety on the surface of the fiber and the hydrophilic solution to cause swelling, leading to gelation of the entire hydrophilic solution.

When a hydrophobic solution such as a hydrophobic solvent and a hydrophobic mixed solution is charged into the lipid peptide-type gelator, the lipid peptide-type gelator assembles with its peptide moiety in Formula (1) arranged inside and with its lipid moiety arranged along the surface via self-assembly to form a tubular secondary assembly, that is, a fiber.

Figure 2:
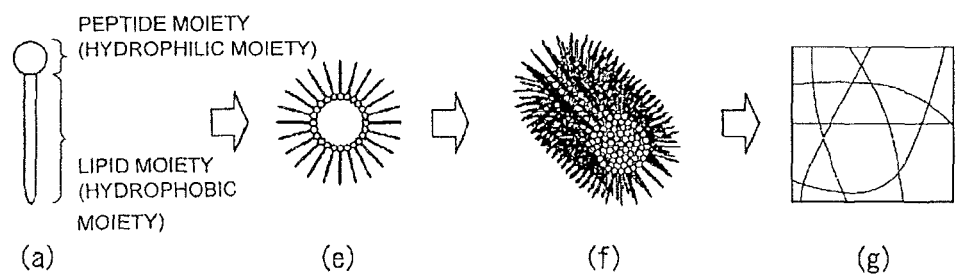
FIG. 2 is a conceptual view of self-assembly and gelation of a lipid peptide-type gelator in a hydrophobic solution.

For reference, a conceptual view of self-assembly and gelation of a low-molecular weight lipid peptide in a hydrophobic solution is exemplified in FIG. 2 (however, not all the low-molecular weight lipid peptides in the present invention necessarily undergo the self-assembly and the gelation shown in FIG. 1). The lipid peptide molecules (a) assemble with each other (e) with their peptide moieties that are hydrophilic moieties arranged inside to form a fiber (f) via self-assembly. The fiber that is formed in a mixed solution forms a three-dimensional network structure (see (g) in FIG. 2, for example), and then a bond is formed between the lipid moiety on the surface of the fiber and the mixed solution to cause swelling, leading to gelation of the entire hydrophobic solution.

The lipid peptide-type gelator for use in the present invention forms a self-assembly in the mixed solution not only when the mixed solution is a gel but also when the mixed solution is a sol or when the addition amount of the lipid peptide-type gelator is insufficient to cause gelation. The cosmetic produced by the production method of a cosmetic according to the present invention can keep the self-assembly even after applied on the skin or the hair. Accordingly, the cosmetic is excellent in stretching on the skin surface and the hair surface, is excellent in permeation into the skin and the hair, has the self-assembly adhering to the skin surface and the hair surface so as to hold the solution and the additional ingredient thereon, and causes no dripping. Furthermore, unlike cosmetics using a polymer or inorganic fine particle gelator, the cosmetic has an excellent shear property and, therefore, is less prone to cause stickiness and crinkles.

[Production Method of Cosmetic]

The production method of a cosmetic according to the present invention for producing a cosmetic in which a polymer thickener is blended in a cosmetic raw material is characterized by blending, in addition to the polymer thickener, at least one of the lipid peptide-type gelators as described above at a ratio of 0.1% by weight to 0.5% by weight based on the mass of the polymer thickener to form a thickening gel.

In the production method of a cosmetic according to the present invention, the concentration of the lipid peptide-type gelator blended is 0.1% by weight to 0.5% by weight, preferably 0.1% by weight to 0.4% by weight, and more preferably 0.1% by weight to 0.3% by weight based on the mass of the polymer thickener blended in the cosmetic raw material, but not particularly limned thereto as long as it is effective.

Examples of the polymer thickener may include polymer thickeners such as polymers, thickeners, and gelators as follows. Among those, carboxyvinyl polymer, carboxymethylcellulose, gellan gum, or xanthan gum is preferred as the polymer thickener.

The concentration of the polymer thickener relative to the concentration of the low-molecular weight lipid peptide is as follows. For example, when the polymer thickener is carboxyvinyl polymer, the concentration of the carboxyvinyl polymer is 0.025% by weight to 0.05% by weight, when the polymer thickener is carboxymethylcellulose, the concentration of the carboxymethylcellulose is 0.05% by weight to 0.1% by weight, when the polymer thickener is gellan gum, the concentration of the gellan gum is 0.05% by weight to 0.1% by weight, and when the polymer thickener is xanthan gum, the concentration of the xanthan gum is 0.05% by weight to 0.1% by weight.

In the production method of a cosmetic according to the present invention, the amounts of the lipid peptide-type gelator and each polymer thickener blended are set in the ranges above to achieve a synergistic effect of the lipid peptide-type gelator and the polymer thickener, which produces a cosmetic in which the use amount of a polymer thickener is significantly reduced when compared with the conventional use amount of a polymer thickener blended in a cosmetic raw material. As a result, increase in viscosity of the cosmetic due to the polymer thickener can be suppressed, so that the cosmetic produced by the production method of a cosmetic according to the present invention can uniformly gel. Furthermore, crinkles or dripping of the cosmetic due to the inclusion of the polymer thickener can be reduced, and the feel in use of the cosmetic can be improved.

[Preparation Method of Gel for Cosmetics]

The preparation method of a gel for cosmetics according to the present invention for preparing a thickening gel for cosmetics is characterized by blending, into an aqueous medium for cosmetics, a polymer thickener and at least one lipid peptide-type gelator that contains a low-molecular weight lipid peptide or a pharmaceutically usable salt thereof at a ratio of 0.1% by weight to 0.5% by weight based on the mass of the polymer thickener to form a gel.

In the preparation method of a gel for cosmetics according to the present invention, the concentration of the lipid peptide-type gelator blended is 0.1% by weight to 0.5% by weight, preferably 0.1% by weight to 0.4% by weight, and more preferably 0.1% by weight to 0.3% by weight based on the mass of the polymer thickener blended in a cosmetic raw material, but not particularly limited thereto as long as it is effective.

Examples of the polymer thickener may include polymer thickeners such as polymers, thickeners, and gelators as follows. Among those, carboxyvinyl polymer, carboxymethylcellulose, gellan gum, or xanthan gum is preferred as the polymer thickener.

The concentration of the polymer thickener relative to the concentration of the low-molecular weight lipid peptide is as follows. For example, when the polymer thickener is carboxyvinyl polymer, the concentration of the carboxyvinyl polymer is 0.025% by weight to 0.05% by weight, when the polymer thickener is carboxymethylcellulose, the concentration of the carboxymethylcellulose is 0.05% by weight to 0.1% by weight, when the polymer thickener is gellan gum, the concentration of the gellan gum is 0.05% by weight to 0.1% by weight, and when the polymer thickener is xanthan gum, the concentration of the xanthan gum is 0.05% by weight to 0.1% by weight.

In the preparation method of a gel for cosmetics according to the present invention, the amounts of the lipid peptide-type gelator and each polymer thickener blended are set in the ranges above to achieve a synergistic effect of the lipid peptide-type gelator and the polymer thickener, thereby the use amount of the polymer thickener is significantly reduced. As a result, increase in viscosity of the cosmetic due to the polymer thickener can be suppressed, so that the gel for cosmetics prepared by the preparation method of a gel for cosmetics according to the present invention can be formed uniformly.

[Method of Reducing Use Amount of Polymer Thickener]

The method of reducing the use amount of a polymer thickener according to the present invention in production of a cosmetic in which a polymer thickener is blended in a cosmetic raw material is characterized by blending, into a cosmetic raw material in addition to the polymer thickener, at least one lipid peptide-type gelator that contains a low-molecular weight lipid peptide or a pharmaceutically usable salt thereof at a ratio of 0.1% by weight to 0.5% by weight based on the mass of the polymer thickener.

In the method of reducing the use amount of a polymer thickener according to the present invention, the concentration of the lipid peptide-type gelator blended is 0.1% by weight to 0.5% by weight, preferably 0.1% by weight to 0.4% by weight, and more preferably 0.1% by weight to 0.3% by weight based on the mass of the polymer thickener blended in a cosmetic raw material, but not particularly limited thereto as long as it is effective.

Examples of the polymer thickener may include polymer thickeners such as polymers, thickeners, and gelators as follows. Among those, carboxyvinyl polymer, carboxymethylcellulose, gellan gum, or xanthan gum is preferred as the polymer thickener.

The concentration of the polymer thickener relative to the concentration of the low-molecular weight lipid peptide is as follows. For example, when the polymer thickener is carboxyvinyl polymer, the concentration of the carboxyvinyl polymer is 0.025% by weight to 0.05% by weight, when the polymer thickener is carboxymethylcellulose, the concentration of the carboxymethylcellulose is 0.05% by weight to 0.1% by weight, when the polymer thickener is gellan gum, the concentration of the gellan gum is 0.05% by weight to 0.1% by weight, and when the polymer thickener is xanthan gum, the concentration of the xanthan gum is 0.05% by weight to 0.1% by weight.

In the method of reducing the use amount of a polymer thickener according to the present invention, the amounts of the lipid peptide-type gelator and each polymer thickener blended are set in the ranges above to achieve a synergistic effect of the lipid peptide-type gelator and the polymer thickener, thereby the use amount of the polymer thickener is significantly reduced when compared with the conventional use amount of a polymer thickener blended in a cosmetic raw material.

The application of the present invention is not limited to the field of cosmetics. Specifically, the present invention can be applied not only in the field of cosmetics but also in the field of medical instruments, for example, such as wound dressing base materials or hemostatic base materials.

For example, when the preparation method of a gel according to the present invention is used in the field of medical instruments, the synergistic effect of the lipid peptide-type gelator and the polymer thickener can significantly reduce the use amount of the polymer thickener to prepare a thickening gel for medical use.

When the method of reducing the use amount of a polymer thickener according to the present invention is used, the synergistic effect of the lipid peptide-type aviator and the polymer thickener can significantly reduce the use amount of the polymer thickener blended in medical instruments in production of medical instruments such as wound dressing base materials or hemostatic base materials.

The cosmetic produced by the production method of a cosmetic according to the present invention may include water, an alcohol, a polyhydric alcohol, a hydrophilic organic solvent, a hydrophobic organic solvent, or a mixed solution of them.

Preferred examples of the water include clean water, purified water, hard water, soft water, natural water, deep sea water, electrolyzed alkaline ionized water, electrolyzed acidic ionized water, ionized water, and cluster water.

The alcohol is a monovalent alcohol, and examples thereof include, but are not particularly limited to, $C_{1-6}$ alcohols that dissolve in water at a certain proportion, specifically methanol, ethanol, 2-propanol, isobutanol, and higher alcohols, specifically oleyl alcohol, phenoxy alcohol.

The polyhydric alcohol is a divalent or a higher-valent alcohol, and examples thereof include propylene glycol, 1,3-butanediol, 2-ethyl-1,3-hexanediol, glycerin, isopentyldiol, ethylhexanediol, erythrulose, ozonized glycerin, caprylyl glycol, glycol, $(C_{15-18})$ glycol, $(C_{20-30})$ glycol, glycerin, diethylene glycol, diglycerin, dithiaoctanediol, DPG, thioglycerin, 1,10-decanediol, decylene glycol, triethylene glycol, trimethylhydroxymethylcyclohexanol, phytantriol, phenoxypropanediol, 1,2-butanediol, 2,3-butanediol, butylethylpropanediol, 1,2-hexanediol, hexylene glycol, pentylene glycol, methylpropanediol, menthane diol, lauryl glycol, and polypropylene glycol.

The hydrophilic organic solvent means an organic solvent, other than the alcohol and the polyhydric alcohol, that dissolves in water at a certain proportion. Examples thereof include acetone, dioxanes, ethyl acetate, and aqua jojoba oil.

The hydrophobic organic solvent means an organic solvent, other than the alcohol, that does not freely dissolve in water. Examples thereof include oils/fats, silicone oils, and ester solvents.

Examples of the oils/fats include castor oil and olive oil.

Examples of the silicone oils include dimethyl silicone oil and methylphenyl silicone oil.

Examples of the ester solvent include propylene glycol alginic acid ester, ethyl acetate, diheptylundecyl adipate, acetylated lanolin, isostearyl glyceryl, and octyldodecyl isostearate.

A solvent used in the cosmetic produced by the production method of a cosmetic according to the present invention is preferably water, an alcohol, a polyhydric alcohol, a hydrophobic solvent, a hydrophilic solvent, a mixed solution of water and one or more selected from the group consisting of alcohols, polyhydric alcohols, oils/fats, silicone oils, and ester solvents, or a mixed solution of a polyhydric alcohol and one or more selected from the group consisting of alcohols, oils/fats, silicone oils, and ester solvents. Water or a solution in which an alcohol or a polyhydric alcohol is dissolved in water is particularly preferred.

The cosmetic produced by the production method of a cosmetic according to the present invention may include, where appropriate, an additional ingredient such as physiologically active substances and functional substances that are generally blended in cosmetics. Examples thereof include oily base materials, moisturizers, tactile-feeling enhancers, surfactants, polymers, thickeners, gelators, solvents, propellants, antioxidants, reducing agents, oxidizing agents, preservatives, antimicrobial agents, antiseptics, chelating agents, pH-adjusting agents, acids, alkalis, powders, inorganic salts, ultraviolet absorbers, skin-brightening agents, vitamins and derivatives thereof, hair growth-promoting agents, blood circulation-promoters, stimulating agents, hormones, anti-wrinkle agents, anti-aging agents, tightening agents, cool-feeling agents, warm-feeling agents, wound-healing promoters, abirritants, analgesics, cell activators, plant, animal, and microbial extracts, antipruritics, keratin-exfoliating/dissolving agents, antiperspirants, refrigerants, styptics, enzymes, nucleic acids, perfumes, coloring, agents, colorants, dyes, pigments, antiphlogistics, anti-inflammatory agents, anti-asthmatic agents, drugs for chronic obstructive pulmonary diseases, antiallergic agents, immunomodulators, anti-infective agents, and antifungal agents.

Examples of these additional ingredients are as follows. Preferred examples of the oily base materials include: higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols such as benzyl alcohol, and derivatives thereof; higher fatty acids such as lauric acid, myristic acid, palmitic acid, stearic acid, isostearic acid, behenic acid, undecylene acid, 12-hydroxystearic acid, palmitoleic acid, oleic acid, linoleic acid, linolenic acid, erucic acid, docosahexaenoic acid, eicosapentaenoic acid, isohexadecanoic acid, anteisohenicosanoic acid, branched long-chain fatty acids, dimer acids, and hydrogenated dimer acids, and metallic soaps such as aluminum salts thereof, calcium salts thereof, magnesium salts thereof, zinc salts thereof, potassium salts thereof, and sodium salts thereof, and nitrogen-containing derivatives such as amides; hydrocarbons such as liquid paraffin (mineral oil), heavy liquid isoparaffin, light liquid isoparaffin, α-olefin oligomers, polyisobutene, hydrogenated polyisobutene, polybutene, squalane, olive squalane, squalene, vaseline, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and ethylene-propylene copolymers: vegetable oils such as coconut oil, palm oil, palm kernel oil, safflower oil, olive oil, castor oil, avocado oil, sesame seed oil, tea oil, evening primrose oil, wheat germ oil, macadamia seed oil, hazelnut oil, kukui nut oil, rose hip oil, meadowfoam oil, persic oil, tea tree oil, mint oil, corn oil, rapeseed oil, sunflower oil, wheat germ oil, linseed oil, cottonseed oil, soybean oil, peanut oil, rice bran oil, cocoa butter, shea butter, hydrogenated coconut oil, hydrogenated castor oil, jojoba oil, and hydrogenated jojoba oil; animal oils/fats such as beef tallow, milk fat, horse fat, egg-yolk oil, mink oil, and turtle oil; animal waxes such as spermaceti, lanolin, and orange roughy oil; lanolins such as liquid lanolin, reduced lanolin, adsorption-purified lanolin, acetylated lanolin, acetylated liquid lanolin, hydroxylated lanolin, polyoxyethylene lanolin, lanolin fatty acid, hard lanolin fatty acid, lanolin alcohol, acetylated lanolin alcohol, and acetylated (cetyl/lanolyl) ester; phospholipids such as lecithin, phosphatidylcholine, phosphatidylethanolamine, phosphatidylserine, phosphatidylglycerol, phosphatidylinositol, sphingophospholipids including sphingomyelin, phosphatidic acid, and lysolecithin; phospholipid derivatives such as hydrogenated soybean phospholipid, partially hydrogenated soybean phospholipid, hydrogenated egg-yolk phospholipid, and partially hydrogenated egg-yolk phospholipid; sterols such as cholesterol, dihydrocholesterol, lanosterol, dihydrolanosterol, phytosterol, and cholic acid; sapogenins; saponins; sterol esters such as cholesteryl acetate, cholesteryl nonancoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl)N-lauroyl-L-glutamate, di(phytosteryl/octyldodecyl) N-lauroyl-L-glutamate, acyl sarcosine alkyl esters including isopropyl N-lauroyl sarcosinate, cholesteryl 12-hydroxystearate, cholesteryl macadamiate, phytosteryl macadamiate, phytosteryl isostearate, soft lanolin fatty acid eholesteryl ester, hard lanolin fatty acid cholesteryl ester, branched long-chain fatty acid cholesteryl esters, and long-chain α-hydroxy fatty acid cholesteryl esters; lipid complexes such as phospholipid-cholesterol complexes and phospholipid-phytosterol complexes; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, caprylic/capric triglyceride, caprylic/capric/myristic/stearic triglyceride, hydrogenated rosin triglyceride (hydrogenated ester gum), rosin triglyceride (ester gum), glyceryl behenate eicosanedioate, trimethylolpropane trioctanoate, trimethylolpropane triisostearate, neopentyl glycol dioctanoate, neopentyl glycol dicaprate, 2-butyl-2-ethyl-1,3-propanediol dioetanoate, propylene glycol dioleate, pentaerythrityl tetraoctanoate, hydrogenated rosin pentaerythrityl ester, ditrimethylolpropane triethylhexanoate, ditrimethylolpropane isostearate/sebacate, pentaerythrityl triethylhexanoate, dipentaerythrityl hydroxysterate/stearate/resinate, diglyceryl diisostearate, polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives such as diisopropyl dimer dilinoleate, diisosteatyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensates, hydrogenated castor oil dimer dilinoleate, and hydroxyalkyl dimer dilinoleyl ether; fatty acid alkanolamides such as coconut oil fatty acid monothanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); silicones such as dimethicone (dimethylpolysiloxane), highly polymerized dimethicone (highly polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyldimethylamine, (aminoethylaminopropyl methicone/dimethicone) copolymer, dimethiconol, dimethiconol crosspolymer, silicone resins, silicone rubber, amino-modified silicones including aminopropyl dimethicone and amodimethicone, cation-modified silicones, polyether-modified silicones including dimethicone copolyols, polyglycerin-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine oils such as perfluorodecane, perfluorooctane, and perfluaropolyether.

Preferred examples of the moisturizers and the tactile-feeling enhancers include: polyols and polymers thereof such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers; glycol alkyl ethers such as diethylene glycol monoethyl ether (ethoxydiglycol), ethylene glycol monoethyl ether, ethylene glycol monobutyl ether, and diethylene glycol dibutyl ether; water-soluble esters such as polyglyceryl-10 (eicosanedioate/tetradecanedioate) and polyglyceryl-10 tetradecanedioate; sugar alcohols such as sorbitol, xylitol, erythritol, mannitol, and maltitol; sugars and derivatives thereof such as glucose, fructose, galactose, mannose, threose, xylose, arabinose, fucose, ribose, deoxyribose, maltose, trehalose, lactose, raffinose, gluconic acid, glucuronic acid, cyclodextrins (α-, β-, and γ-cyclodextrins, and modified cyclodextrins such as maltosyl cyclodextrin and hydroxyalkyl cyclodextrin), β-glucan, chitin, chitosan, heparin and heparin derivatives, pectin, arabinogalactan, dextrin, dextran, glycogen, ethyl glucoside, poly(glucosylethyl methacrylate), and (glucosylethyl methacrylate) copolymer; hyaluronic acid and sodium hyaluronate; sodium chondroitin sulfate; mucoitin sulfate, charonin sulfate, kerato sulfate, and dermatan sulfate; Tremella fuciformis extract and Tremella fuciformis polysaccharide; fucoidan; tuberose polysaccharide and natural polysaccharides; organic acids such as citric acid, tartaric acid, and lactic acid, and salts thereof; urea and derivatives thereof; 2-pyrrolidone-5-carboxylic acid, and salts thereof including a sodium salt thereof: amino acids such as betaine (trimethylglycine), proline, hydroxyproline, arginine, lysine, serine, glycine, alanine, phenylalanine, tyrosine, β-alanine, threonine, glutamic acid, glutamine, asparagine, aspartic acid, cysteine, cysteine, methionine, leucine, isoleucine, valine, tryptophan, histidine, and taurine, and salts thereof; protein peptides, and derivative thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides such as palmitoyl oligopeptide, palmitoyl pentapeptide, and palmitoyl tetrapeptide; silylated peptides; a culture solution of lactic acid bacteria, a yeast extract solution, an eggshell membrane protein, bovine submaxillary mucin, hypotaurine, sesame lignan glycoside, glutathione, albumin, and whey; choline chloride and phosphoryl choline; and animal and plant extract components such as a placenta extract solution, elastin, collagen, aloe extract. Hamamelis virginiana water, Luffa cylindrica water, Chamomilla recutita extract, licorice extract, Symphytum officinale extract, silk extract, Rosa roxburghii extract. Achillea millefolium extract, Eucalyptus globulus extract, and Melilotus officinalis extract, and ceramides such as natural ceramides (types 1, 2, 3, 4, 5, and 6), hydroxyceramide, pseudoceramide, sphingoglycolipid, ceramide-containing extracts, and glucosylceramide-containing extracts.

Preferred examples of the surfactants include anionic surfactants, nonionic surfactants, cationic surfactants, amphoteric surfactants, and polymer surfactants. Preferred examples of the surfactants are as follows. Preferred examples of the anionic surfactants include: fatty acid salts such as potassium laurate and potassium myristate; alkyl sulfuric acid ester salts such as sodium lauryl sulfate, triethanolamine lauryl sulfate, and ammonium lauryl sulfate; polyoxyethylene alkyl sulfates such as sodium laureth sulfate and triethanolamine laureth sulfate; acyl N-methyl amino acid salts such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methytalaninate; acylamino acid salts such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates such as glycerin hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctyl sulfosuccinate: alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkylbenzene sulfonates such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetates; alkyl ether phosphoric acid ester salts such as sodium laureth phosphate, sodium dilaureth phosphate, sodium trilaureth phosphate, and sodium monooreth phosphate; alkyl phosphoric acid ester salts such as potassium lauryl phosphate; sodium caseinate; alkyl aryl ether phosphates; fatty amide ether phosphates; phospholipids such as phosphatidylglycerol, phosphatidylinositol, and phosphatidic acid; and silicone anionic surfactants such as carboxylic acid-modified silicones, phosphoric acid-modified silicones, and sulfuric acid-modified silicones. Preferred examples of the nonionic surfactants include: polyoxyethylene alkyl ethers with various addition numbers of polyoxyethylenes such as laureths (polyoxyethylene lauryl ethers), ceteths (polyoxyethylene cetyl ethers), steareths (polyoxyethylene stearyl ethers), beheneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylerte-polyoxypropylene glycerin ether; polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl cocoate, glycerin mono-cottonseed oil fatty acid ester, glycerin monoerucate, glycerin sesquioleate, glycerin α, α'-oleate pyroglutamate, and glycerin monostearate malate; polyglycerin fatty acid esters such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl- 0 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters such as ethylene glycol monostearate; propylene glycol mono-fatty acid esters such as propylene glycol monostearate; pentaerythritol fatty acid partial esters; sorbitol fatty acid partial esters; maltitol fatty acid partial esters; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethythexylate diglycerol, and sorbitan tetra-2-ethythexylate diglycerol; sugar derivative partial esters such as sucrose fatty acid esters, methyl glucoside fatty acid esters, and trehalose undecylenoate; alkyl glucosides such as caprylyl glucoside; alkyl polyglycosides; lanolin alcohol; reduced lanolin; polyoxyethylene fatty acid monoesters and polyoxyethylene fatty acid diesters such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters such as polyoxyethylene monooleates including polyoxyethylene glycerin monostearate, polyoxyethylene glycerin monoisostearate, and polyoxyethylene glycerin triisostearate; polyoxyethylene sorbitan fatty acid esters such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol. fatty acid esters such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene animal and vegetable oils/fats such as polyoxyethylene sorbitol beeswax; alkyl glyceryl ethers such as isostearyi glyceryl ether, chitnyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants such as saponins and sophorolipid; polyoxyethylene fatty acid amides; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), laurie acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); alkyl dimethylamine oxides such as lauramine oxide, cocamine oxide, stearamine oxide, and behenamine oxide; alkyl ethoxy dimethylamine oxides; polyoxyethylene alkyl mercaptans; and silicone nonionic surfactants such as polyether-modified silicones including dimethicone copolyols, polysiloxane-oxyalkylene copolymers, polyglycerin-modified silicones, and sugar-modified silicones. Preferred examples of the cationic surfactants include: alkyl trimethylammonium chlorides such as behentrimonium chloride, steartrimonium chloride, cetrimonium chloride, and lauryltrimonium chloride; alkyl trimethylammonium bromides such as steryltrimonium bromide; dialkyl dimethylammonium chlorides such as distearyldimonium chloride and dicocodimonium chloride; fatty acid amide amines such as stearamide propyldimethylamine and stearamide ethyldiethylamine, and salts thereof; alkyl ether amines such as stearoxypropyldimethylatnine, and salts and quaternary salts thereof; fatty acid amide quaternary ammonium salts such as branched long-chain fatty acid (12 to 31) aminopropylethyldimethylammonium ethyl sulfates and lanolin fatty acid aminopropylethyldimethylammonium ethyl sulfate; polyoxyethylene alkylamines, and salts and quaternary salts thereof; alkylamine salts; fatty acid amide guanidium salts; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone cationic surfactants such as amino-modified silicones including aminopropyl dimethicone and amodimethicone, cation-modified silicones, cation-modified and polyether-modified silicones, and amino-modified and polyether-modified silicones. Preferred examples of the amphoteric surfactants include: N-alkyl-N, N-dimethylamino acid betaines such as lauryl betaine (lauryl dimethylaminoacetic acid betaine); fatty acid amide alkyl-N,N-dimethylamio acid betaines such as cocamide propyl betaine and lauramide propyl betaine; imidazoline-type betaines such as sodium cocoamphoacetate and sodium lauroamphoacetate; alkyl sulfobetaines such as alkyl dimethyltaurines; sulfuric acid-type betaines such as alkyl dimethylamino ethanol sulfuric acid esters; phosphoric acid-type betaines such as alkyl dimethylamino ethanol phosphoric acid esters; phospholipids such as phosphatidylcholine, phosphatidylethanolamine, phosphatidylserine, sphingophospholipids including sphingomyelin, lysolecithin, hydrogenated soybean phospholipid, partially hydrogenated soybean phospholipid, hydrogenated egg-yolk phospholipid, partially hydrogenated egg-yolk phospholipid, and hydroxylated lecithin; and silicone amphoteric surfactants. Preferred examples of the polymer surfactants include: polyvinyl alcohol, sodium alginate, starch derivatives, gum tragacanth, and acrylic acid-alkyl methacrylate copolymers; and various silicone surfactants.

Preferred examples of the polymers, the thickeners, and the gelators include: guar gum, locust bean gum, quince seed, carrageenan, galactan, gum arabic, tara gum, tamarind, furcelleran, karaya gum, Abelmoschus manihot, cara gum, gum tragacanth, pectin, pectic acid and salts thereof including a sodium salt thereof, alginic acid and salts thereof including a sodium salt thereof, and mannan; starchs such as rice starch, corn starch, potato starch, and wheat starch; xanthan gum, dextran, succinoglucan, curdlan, hyaluronic acid, and salts thereof, xanthan gum, pullulan, gellan gum, chitin, chitosan, agar-agar, brown algae extract, chondroitin sulfate, casein, collagen, gelatin, and albumin; cellulose and derivatives thereof such as methylcellulose, ethylrellulose, hydroxyethylcellulose, hydroxypropylcellulose, carboxymethylcellulose and salts thereof including sodium salts thereof, methylhydroxypropylcellulose, sodium cellulose sulfate, dialkyl dimethvlammonium sulfate cellulose, crystalline cellulose, and cellulose powder; starch derivatives such as soluble starch, starch polymers including carboxymethyl starch, methylhydroxypropyl starch, and methyl starch, starch hydroxypropyltrimonium chloride, and aluminum corn starch octenylsuccinate; alginic acid derivatives such as sodium alginate and propylene glycol alginic acid ester; polyvinylpyrrolidone (PVP), polyvinyl alcohol (PVA), vinylpyrrolidone-vinyl alcohol copolymers, and polyvinyl methyl ether; polyethylene glycol, polypropylene glycol, and polyoxyethylene-polyoxypropylene copolymers; amphoteric methacrylic acid ester copolymers such as (methacryloyloxyethylcarboxy betaine/alkyl methacrylate) copolymers and (acrylate/stearyl actylate/ethylamine oxide methacrylate) copolymers; (dimethicone/vinyl dimethicone) crosspolymer, (alkyl acrylate/diacetone acrylamide) copolymer, and (alkyl acrylate/diacetone acrylamide) copolymers AMP; partially saponified polyvinyl acetate and maleic acid copolymers; vinylpyrrolidone-dialkyl aminoalkyl methacrylate copolymers; acrylic resin alkanolamines; polyesters and water-dispersable polyesters; polyacrylamides; polyacrylic acid ester copolymers such as ethyl polyacrylate, carboxyvinyl polymers, polyacrylic acid and salts thereof including a sodium salt thereof, acrylic acid-methacrylic acid ester copolymers; acrylic acid-alkyl methacrylate copolymers; cationized celluloses such as polyquaternium-10, diallyldimethylammonium chloride-acrylamide copolymers such as polyquatemium-7, acrylic acid-diallyldimethylammonium chloride copolymers such as polyquaternium-22, acrylic acid-diallyldimethylammonium chloride-acrylamide copolymers such as polyquaternium-39, acrylic acid-canonized methacrylic acid ester copolymers, acrylic acid-cationized methacrylic acid amide copolymers, acrylic acid-methyl acrylate-methacrylamide propyltrimethylammonium chloride copolymers such as polyquaternium-47, and methacryloyl chloride choline ester polymers; cationized polysaccharides such as canonized oligosaccharides, canonized dextran, and guar hydroxypropyltrimonium chloride; polyethyleneimines; cationic polymers; polymers of 2-methacryloyloxyethylphosphorylcholine such as polyquaternium-51, and copolymers thereof with butyl methacrylate copolymer and the like; polymer emulsions such as acrylic resin emulsions, ethyl polyacrylate emulsions, polyacrylic alkyl ester emulsions, polyvinyl acetate resin emulsions, natural rubber latex, and synthetic latex; nitrocellulose; polyurethanes and various copolymers thereof; various silicones; various silicone copolymers such as acrylic-silicone graft copolymers; various fluorine polymers; 12-hydroxystearic acid and salts thereof; dextrin fatty acid esters such as dextrin palmitate and dextrin myristate; and silicic anhydride, fumed silica (silicic anhydride ultrafine particles), magnesium aluminum silicate, magnesium sodium silicate, metallic soaps, metal dialkyl phosphates, bentonite, hectorite, organo-modified clay mineral, sucrose fatty acid esters, and fructooligosaccharide fatty acid esters.

Preferred examples of the solvents and the propellants include: lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyldiol; glycol ethers such as diethylene glycol monoethyl ether (ethoxydiglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon and next-generation fron; and propellants such as LPG, dimethyl ether, and carbonic acid gas.

Preferred examples of the antioxidants include: tocopherol (vitamin E) and tocopherol derivatives such as tocopherol acetate; BHT and BHA; gallic acid derivatives such as propyl gallate: vitamin C (ascorbic acid) and/or derivatives thereof, erythorbic acid and derivatives thereof; sulfites such as sodium sulfite; hydrogen sulfites such as sodium hydrogen sulfite; thiosulfates such as sodium thiosulfate: hydrogen metasulfites; thiotaurine and hypotaurine; and thioglycerol, thiourea, thioglycolic acid, and cysteine hydrochloride.

Preferred examples of the reducing agents include thioglycolic acid, cysteine, and cysteamine.

Preferred examples of the oxidizing agents include a hydrogen peroxide solution, ammonium persulfate, sodium bromate, and percarbonic acid.

Preferred examples of the preservatives, the antimicrobial agents, and the antiseptics include: hydroxybenzoic acids and salts and esters thereof such as methylparaben, ethylparaben, propylparaben, and butylparaben; salicylic acid; sodium benzoate; phenoxyethanol; 1,2-diols such as 1,2-pentanediol and 1,2-hexanediol; isothiazolinone derivatives such as methylchloroisothiazolinone and methylisothiazolinone; imidazolinium urea; dehydroacetic acid and salts thereof: phenols; halogenated bisphenols such as triclosan, acid amides, and quaternary ammonium salts; trichlorocarbanilide, zinc pyrithione, benzalkonium chloride, benzethonium chloride, sorbic acid, chlorhexidine, chlorhexidine gluconate, halocarban, hexachlorophene, and hinokitiol; phenol and other phenols such as isopropylphenol, cresol, thymol, p-chlorophenol, phenylphenol, and sodium phenylphenolate; and phenylethyl alcohol, Kankoso, antimicrobial zeolite, and a silver ion.

Preferred examples of the chelating agents include: edetates (ethylenediamine tetraacetates) such as EDTA, EDTA-Na2, EDTA-Na3, and EDTA-Na4; hydroxyethylethylenediaminetriacetates such as HEDTA-Na3; pentetates (diethylenetriaminepentaacetate); phytic acid, phosphonic acids such as etidronic acid, and salts thereof including sodium salts thereof; sodium oxalate; polyamino acids such as polyaspartic acid and polyglutamic acid; sodium polyphosphate, sodium metaphosphate, and phosphoric acid; and sodium citrate, citric acid, alanine, dihydroxyethylglycine, glucortic acid, ascorbic acid, succinic acid, and tartaric acid.

Preferred examples of the pH-adjusting agents, acids, and alkalis include: citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, an aqueous ammonia solution, guanidine carbonate, and ammonium carbonate.

Preferred examples of the powders include: inorganic powders of various sizes and shapes such as mica, talc, kaolin, sericite, montmorillonite, kaolinite, isinglass, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfite, calcium phosphate, fluorapatite, hydroxyapatite, ceramic powder, bentonite, smectite, clay, mud, metallic soaps (zinc myristate, calcium palmitate, and aluminum stearate, for example), calcium carbonate, red iron oxide, yellow iron oxide, black iron oxide, ultramarine, prussian blue, carbon black, titanium oxide, titanium oxide fine particles and titanium oxide ultra fine particles, zinc oxide, zinc oxide fine particles and zinc oxide ultratine particles, alumina, silica, fumed silica (silicic anhydride ultrafine particles), titanated mica, fish scale guanine, boron nitride, photochromic pigments, synthetic fluorophlogopite, fine-particle composite powders, gold, and aluminum, and these inorganic powders that are treated with a silicone such as hydrogen silicone and cyclic hydrogen silicone or are otherwise treated with various surface-treating agents such as silane coupling agents and titanium coupling agents to hydrophobize or hydrophilize these inorganic powders; and organic powders, surface-treated powders, and organic-inorganic composite powders of various sizes and shapes such as starch, cellulose, nylon powder, polyethylene powder, polymethyl methacrylate powder, polystyrene powder, styrene/acrylate copolymer resin powder, polyester powder, benzoguanamine resin powder, polyethylene terephthalate/polymethyl methacrylate-laminated powder, polyethylene terephthalate/aluminum/epoxy-laminated powder, urethane powder, silicone powder, and Teflon (registered trademark) powder.

Preferred examples of the inorganic salts include sodium chloride-containing salts such as common salt, regular salt, rock salt, sea salt, and natural salt; potassium chloride, aluminum chloride, calcium chloride, magnesium chloride, bittern, zinc chloride, and aminomum chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and trisodium phosphates, potassium phosphates, calcium phosphates, and magnesium phosphates.

Preferred examples of the ultraviolet absorbers include benzoate-based ultraviolet absorbers such as p-aminobenzoic acid, p-aminobenzoic acid monoglycerin ester, N,N-dipropoxy p-aminobenzoic acid ethyl ester, N,N-diethoxy p-aminobenzoic acid ethyl ester, N,N-dimethyl p-aminobenzoic acid ethyl ester. N,N-dimethyl p-aminobenzoic acid butyl ester, and N,N-dimethyl p-aminobenzoic acid ethyl ester; anthranilate-based ultraviolet absorbers such as homomenthyl-N-acetylanthranilate, salicylate-based ultraviolet absorbers such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl eliminate, propyl-p-methoxy cinnamate, isopropyl-p-methoxy cinnamate, isoamyl-p-methoxy cinnamate, 2-ethylhexyl p-methoxy cinnamate (octyl p-methoxy cinnamate), 2-ethoxyethyl-p-methoxy cinnamate (cinoxate), cyclohexyl-p-methoxy cinnamate, ethyl-α-cyano-β-phenyl cinnamate, 2-ethylhexyl α-cyano-β-phenyl cinnamate (octocrylene), glyceryl mono-2-ethylhexanoyl-di-p-methoxy cinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzalazines; dianisoylmethane; 5-(3,3-dimethyl-2-norbomylidene)-3-pentan-2-one; dibenzoylmethane derivatives such as 4-t-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and orizanol and derivatives thereof.

Preferred examples of the skin-brightening agents include hydroquinone glycosides such as arbutin and α-arbutin, and esters thereof; ascorbic acid and ascorbic acid derivatives such as ascorbyl phosphate salts including sodium ascorbyl phosphate and magnesium ascorbyl phosphate, ascorbyl fatty acid esters including ascorbyl tetraisopalmitate, ascorbic acid alkyl ethers including ascorbic acid ethyl ether, ascorbyl glucosides including ascorbyl 2-glucoside and fatty acid esters thereof, ascorbyl sulfurate, and tocopheryl ascorbyl phosphate; and kojic acid, ellagic acid, tranexamic acid and derivatives thereof, ferulic acid and derivatives thereof; placenta extract, glutathione, orizanol, butyl resorcinol, and plant extracts such as oil-soluble Chamomilla recutita extract, oil-soluble licorice extract, Seikaryu extract, and Saxifraga sarmentosa extract.

Preferred examples of the vitamins and derivatives thereof include vitamin As such as retinol, retinal acetate, and retinol palmitate; vitamin Bs such as thiamine hydrochloride, thiamine sulfate, riboflavin, riboflavin acetate, pyridoxine hydrochloride, pyridoxine dioctanoate, pyridoxine dipalmitate, fiavin adenine dinucleotide, cyanocobalamins, folic acids, nicotinic acids such as nicotinamide and benzyl nicotinate, and cholines; vitamin Cs such as ascorbic acid and salts thereof including a sodium salt thereof; vitamin Ds; vitamin Es such as α-, β-, γ-, and δ-tocopherols; other vitamins such as pantothenic acid and biotin; ascorbic acid derivatives such as ascorbyl phosphate salts including sodium ascorbyl phosphate and magnesium ascorbyl phosphate, ascorbyl fatty acid esters including ascorbyl tetraisopalmitate, ascorbyl stearate, ascorbyl palmitate, and ascorbyl dipalmitate, ascorbic acid alkyl ethers including ascorbic acid ethyl ether, ascorbyl glucosides including ascorbyl 2-glucoside and fatty acid esters thereof, and tocopheryl ascorbyl phosphate; and vitamin derivatives such as tocopherol derivatives including tocopherol nicotinate, tocopherol acetate, tocopherol Inioleate, tocopherol ferulate, and tocopherol phosphate, tocotrienol, and other various vitamin derivatives.

Preferred examples of the hair growth-promoting agents, the blood circulation-promoters, and the stimulating agents include plant extracts and tinctures such as Swertia herb extract, Capsicum frutescens tincture, ginger tincture, ginger extract, and cantharides tincture; and capsaicin, nonylic acid vanillylamide, zingerone, ichthammol, tannic acid, borneol, cyclandelate, cinnarizine, tolazoline, acetylcholine, verapamil, cepharanthine, γ-orizanol, vitamin E and derivatives thereof including tocopherol nicotinate and tocopherol acetate, γ-orizanol, nicotinic acid and derivatives thereof including nicotinamide, benzyl nicotinate, inositol hexanicotinate, and nicotinic alcohol, allantoin, Kankoso 301, Kankoso 401, carpronium chloride, pentadecanoic acid monoglyceride, flavanonol derivatives, stigmasterol and stigmastanol and glycosides thereof; and minoxidil.

Preferred examples of the hormones include estradiol, estrone, ethynylestradiol, cortisone, hydrocortisone, and prednisone.

Preferred examples of other substances with drug efficacy such as the anti-wrinkle agents, the anti-aging agents, the tightening agents, the cool-feeling agents, the warm-feeling agents, the wound-healing promoters, the abirritants, the analgesics, and the cell activators include retinols, retinoic acids, and tocopheryl retinoate; lactic acid, glycolic acid, gluconic acid, fruit acid, and salicylic acid and derivatives thereof including glycosides thereof and esters thereof, and α- and β-hydroxy acids and derivatives thereof such as hydroxycapric acid, lone-chain α-hydroxy fatty acids, long-chain α-hydroxy fatty acid cholesteryl esters; γ-aminobutyric acid and γ-amino-β-hydroxybutytic acid; carnitine; carnosine; creatine; ceramides and sphingosines; caffeine, xanthine, and the like and derivatives thereof; antioxidizing agents and active oxygen scavengers such as coenzyme Q10, carotin, lycopene, astaxanthin, lutein, α-lipoic acid, colloidal platinum nanoparticles, and fullerenes; catechins; flavones such as quercetin; isoflavones; gallic acid and sugar ester derivatives thereof; polyphenols such as tannin, sesamin, proanthocyanidin, chlorogenic acid, and apple polyphenol; rutin and derivatives thereof including glycosides thereof; hesperidin and derivatives thereof including glycosides thereof; lignin glycoside; licorice extract-related substances such as glabridin, glabrene, liquiritin, and isoliquiritin; lactoferrin; shogaol and gingerol; perfume substances such as menthol and cedrol, and derivatives thereof; capsaicin, vanillin, and the like and derivatives thereof; insect repellents such as diethyltoluamide, and complexes of physiologically active substances and cyclodextrins.

Preferred examples of the plant, animal, and microbial extracts include extracts such as iris extract, Angelica keiskei extract, Thujopsis dolabrata extract, asparagus extract, avocado extract. Hydrangea serrata extract, almond extract, Althaea officinalis extract, Arnica montana extract, aloe extract, apricot extract, apricot kernel extract, Gingko biloba extract, Artemisia capillaris flower extract, fennel seed extract, tumeric root extract, oolong tea extract, Arctostaphylos uva-ursi leaf extract, Rosa multiflora fruit extract, Echinacea angustifolia leaf extract, Isodonis japonicus extract, Scutellaria baicalensis extract, Phellodendron amurense bark extract, Coptis japonica root extract, Hordeum vulgare extract, Panax ginseng extract, Hypericum perforatum extract Lamium album extract, Ononis spinosa extract, Nasturtium officinale extract, orange extract, dried sea water residues, seaweed extract, Persimmon leaf extract, Pyracantha fortuneana extract, hydrolyzed elastin, hydrolyzed wheat powder, hydrolyzed silk, Pueraria lobata root extract, Chamomilla recutita extract, oil-soluble Chamomilla recutita extract. Daucus carota sativa extract, Artemisia capillaris extract, Avena fatua extract, carcade extract, licorice extract, oil-soluble licorice extract, kiwi fruit extract, kiou extract, Auricularia auricula-judae extract, Cinchona succirubra extract, cucumber extract, Paulownia tomentosa leaf extract, guanosine, guava extract. Sophora angustifolia extract, Gardenia florida extract, Sasa veitchii extract, Sophora angustifolia extract, walnut extract, chestnut extract, grapefruit extract, Clematis vitalba extract, Oryza sativa Linne extract, black sugar extract, black vinegar, Chlorella vulgaris extract, Morus alba extract, Gentiana lutea extract, Geranium thunbergii extract, black tea extract, yeast extract, magnolia bark extract, coffee seed extract, Arctium lappa root extract, rice extract, fermented rice extract, fermented rice bran extract, rice germ oil, Symphytum officinale extract, collagen, Vaccinium vitis-idaea extract, Asarum sieboldi extract, Bupleurum falcatum extract, umbilical extract, saffron extract, salvia extract, Saponaria officinalis extract, sasa extract, Crataegus cuneata fruit extract, Bombyx mori excrementum extract, Zanthoxylum piperitum extract, Corthellus shiitake extract, Rehmannia glutincisa extract, Lithospermum erythrorhizon root extract, Perilla ocymoides extract, Tilia cordata extract, Spiraea ulmaria extract, jatoba extract, Paeonia albiflora extract, ginger extract. Acorus calamus root extract, Betula Platyphylla Japonica extract, Tremella fuciformis extract, Equisetum arvense extract, stevia extract, stevia fermentation product, Seikaryu extract, Hedera helix extract, Crataegus oxyacantha extract, Sambucus nigra extract, Achillea millefolium extract, Mentha piperita extract, sage extract, Malva sylvestris extract, Cnidium officinale extract, Swertia herb extract, Morus alba root extract, Rheum extract, soybean extract, Zizyphus jujuba extract, thyme extract, dandelion extract, lichen extract, Camellia sinensis leaf extract, clove extract, Imperata cylindrica extract, Citrus unshiu peel extract, tea tree oil, Rubus suavissimus extract, Capsicum frutescens extract, Angelica acutiloba extract, Calendula officinalis extract, Prunus persica kernel extract, Citrus aurantium amara peel extract, Houttuynia cordata extract, tomato extract, natto extract, carrot extract, garlic extract, Rosa canina extract, hibiscus extract, Ophiopogon japonicus root extract, Nelumbo nucifera extract, parsley extract, birch extract, honey, Hamamelis virginiana extract, Parietaria officinalis extract, Isodonis japonicus extract, bisabolol, Chamaecyparis obtusa extract, Bifidobacterium extract, Eriobotrya japonica extract, Tussilago farfara extract, Petasites japonicus flower stalk extract, Poria cocos sclerotium extract, Ruscus aculeatus extract, grape extract, grape seed extract, propolis, Luffa cylindrica extract, safflower extract, peppermint extract, Tilia miqueliana extract, Paeonia suffruticosa root extract, hops extract, Rosa rugosa flower extract, Pinus sylvestris cone extract, horse chestnut extract, Lysichiton camtschatcense extract, Sapindus mukurossi peel extract, Melissa officinalis extract, Nemacystus decipiens extract, peach extract, Centaurea cyanus extract, Eucalyptus globulus extract, Saxifraga sarmentosa extract, Citrus junos extract, lily extract, Coix lacryma-jobi seed extract, Artemisia princeps extract, lavender extract, green tea extract, egg shell membrane extract, apple extract, rooibos tea extract, Ganoderma lucidum extract, lettuce extract, lemon extract, forsythia extract, Astragalus sinicus extract, rose extract, rosemary extract, Anthemis nobilis extract, royal jelly extract, and Sanguisorba officinalis root extract.

Examples of the antipruritics include diphenhydramine hydrochloride, chlorpheniramine maleate, camphor, and a substance P inhibitor.

Examples of the keratin-exfoliating/dissolving agents include salicylic acid, sulfur, resorcin, selenium sulfide, and pyridoxine.

Examples of the antiperspirants include aluminum chlorohydrate, aluminum chloride, zinc oxide, and zinc p-phenolsulfonate.

Examples of the refrigerants include menthol and methyl salicylate.

Examples of the styptics include citric acid, tartaric acid, lactic acid, aluminum potassium sulfate, and tannic acid.

Examples of the enzymes include superoxide dismutases, catalases, lysozyme chloride, lipases, papain, pancreatin, and proteases.

Preferred examples of the nucleic acids include ribonucleic acid and salts thereof, deoxyribonucleic acid and salts thereof, and adenosine triphosphate disodium.

Preferred examples of the perfumes include synthetic perfumes and natural perfumes such as acetyl cedrene, amylcinnamaldehyde, allylamyl glycolate, β-ionone, Iso E Super, isobutylquinoline, iris oil, irone, indole, ylang-ylang oil, undecanal, undecanal, γ-undecalactone, estragole, eugenol, oakmoss, opoponax resinoid, orange oil, eugenol, aurantiol, galacsolid, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmin lactone, cis-jasmone, citral, citronellol, citronellal, cinnamon bark oil, 1.8-cineole, cinnamaldehyde, styrax resinoid, cedarwood oil, cedrene, cedrol, celery seed oil, thyme oil, damascone, dainascenone, thymol, tuberose absolute, decanal, decalactone, terpineol, γ-terpinen, triplal, nerol, nonanal, 2,6-nonadienal, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methyl nonyl acetaldehyde, γ-methyl ionone, menthol, L-menthol, L-menthone, Eucalyptus globulus oil, γ-ionone, lime oil, lavender oil, D-limonene, linalool, lyral, lilial, lemon oil, rose absolute, rose oxide, rose oil, rosemary oil, and various essential oils, and various perfume blends.

Preferred examples of the coloring agents, the colorants, the dyes, and the pigments include legal pigments such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1 Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red NO. 232, Red No. 3, Red No, 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes such as Acid Red No. 14; basic dyes such as Arianor Sienna Brown, Arianor Madder Red, Arianor Steel Blue, and Arianor Straw Yellow; nitro dyes such as HC Yellow No. 2, HC Yellow No. 5, HC Red No. 3,4-hydroxypropylamino-3-nitrophenol, N,N'-bis(2-hydroxyethyl)-2-nitro-p-phenylenediamine, HC Blue No. 2, and Basic Blue No. 26; disperse dyes; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ochre; inorganic black pigments such as black iron oxide and low-dimensional titanium oxide; inorganic violet pigments such as mango violet and cobalt violet; inorganic green pigments such as chromium oxide, chromium hydroxide, and cobalt titanium oxide; inorganic blue pigments such as ultramarine and prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metallic powder pigments such as aluminum powder, copper powder, and gold; surface-treated inorganic and metallic powder pigments; organic pigments such as zirconium lake, barium lake, and aluminum lake; surface-treated organic pigments; natural coloring rents and natural dyes such as astaxanthin, anthraquinones including alizarin, anthocyanidine, β-carotin, catenal, capsanthin, chalcone, carthamin, quercetin, crocin, chlorophyll, curcumin, cochineal, naphthoquinones including shikonin, bixin, flavones, betaeyanidine, henna, hemoglobin, lycopene, riboflavin, and rutin; oxidation dye intermediates and couplers such as p-phenylenediamine, toluene-2,5-diamine, o-, m-, and p-aminophenols, m-phenylenediamine, 5-amino-2-methyl phenol, resorcin, 1-naphthol, 2,6-diaminopyridine, and the like, and salts thereof; autooxidizable dyes such as indoline; and dihydroxyacetone.

Other than these, known cosmetic ingredients such as ingredients described in The Japanese Standards of Cosmetic Ingredients, Japanese Cosmetic Ingredients Codex, Japanese Cosmetic Labeling Name list issued by Japan Cosmetic Industry Association, INCI dictionary (The International Cosmetic Ingredient Dictionary and Handbook) and Japanese and foreign patent publications and patent application publications (including Japanese Translations of PCT International Applications and Domestic Re-Publications of PCT International Applications) categorized as International Patents Classification IPC of A61K7 and A61K8 can be included in a known combination and in a known formulation ratio or in a known formulation amount.

As publicly and commercially available cosmetics, facial cleansers, body washes, makeup removers, and the like are produced by adding, for example, a surfactant and a disinfectant as a cleansing component, an oily base material such as polyhydric alcohols and fatty acid esters as an emollient component, a moisturizer., an oily base material, and a thickener as a moisturizing component, and an antiphlogistic as a rough skin-ameliorating component, and by further adding a preservative, a stabilizer, and the like. A powder can be further added to adjust the viscosity.

Lotions, cosmetic fluids, and the like are produced by adding, for example, water and an inorganic salt as a base component, an oily base material such as polyhydric alcohols and fatty acid esters and a plant extract as a moisturizing component, a thickener, an antiphlogistic as a rough skin-ameliorating component, and vitamins, a skin-brightening agent, an antioxidant, an anti-wrinkle agent, an anti-aging agent, a tightening agent, or the like as a functional component.

Creams are produced by adding, for example, water and a gelator as a base component, an oily base material such as polyhydric alcohols and fatty acid esters as an emollient component, a moisturizer, an oily base material, and a thickener as as moisturizing component, an emulsifier, and an antioxidizing agent or the like as a functional component.

Eye products and the like are produced by adding, for example, water as a base component, an oily base material such as silicone oils, vegetable oils, and fatty acid esters as an emollient component, a moisturizer such as polyhydric alcohols as a moisturizing component, a thickener, an emulsifier, and an antioxidizing agent or the like as a functional component.

Base makeup products, lip rouge, and the like are produced by adding, for example, water and an inorganic salt as a base component, an oily base material such as silicone oils, fatty acid esters, polyhydric alcohols, and fatty acids as an emollient component, an oily base material such as polyhydric alcohols and a moisturizer as a moisturizing component, and a pigment.

Blusher, powdery foundations, and the like are produced by adding, for example, a gelator and an inorganic salt as a base component, a thickener as an emollient component, a pigment, an essential oil, and a powder.

Nail color removers and the like are produced by adding, for example, an oily base material such as esters as a base component, an oily base material such as oils/fats as an emollient component, and a thickener.

UV care performance can be provided to these products by adding a hydrocarbon and a wax as an antioxidizing agent, an inorganic salt and a powder as an ultraviolet-scattering component, an ultraviolet absorber, and the like.

The lipid peptide-type gelator for use in the present invention, which works as a gelator and a thickener in a cosmetic, can replace the gelators and/or the thickeners in these conventional, commercially available cosmetics to increase the safety and the feel in use of these conventional cosmetics.

Examples of the cosmetic produced by the production method of a cosmetic according to the present invention include, but are not limited to, basic care products, makeup products body cosmetics, fragrance cosmetics, and hair care products. However, the cosmetics are not limited to these examples.

The basic care products refer to facial cleansers, makeup removers, lotions, milk lotions, cosmetic fluids, facial creams, facial packs, eye cosmetics, and other facial skin care products.

Examples thereof include facial cleansers such as bar soaps, foaming cleansers, powder cleansers, and sheet cleansers; makeup removers such as foaming makeup removers, cream-type makeup removers, milk-type makeup removers, lotion-type makeup removers, gel-type makeup removers, oil-type makeup removers, and mask-type makeup removers; lotions such as liposome lotions, moisturizing toners, astringent lotions, cleanser lotions, and multi-layered lotions; milk lotions such as emollient lotions, moisturizing lotions, milky lotions, nourishing lotions, nourishing milk lotions, skin moisturizers, moisturizing emulsions, massage lotions, and facial keratin smoothers; cosmetic fluids such as liposome lotions, moisturizing fluids, brightening fluids, and anti-UV fluids; creams such as emollient creams, enriched creams, nourishing creams, vanishing creams, moisturizing creams, night creams, massage creams, cream-type makeup removers, makeup creams, base creams, shaving creams, and facial keratin-softening creams; facial packs such as peel off-type facial packs, powder-type facial packs, wash off-type facial packs, oil-type facial packs, and mask-type makeup removers; eye cosmetics such as eye serums, eye gels, and eye creams; UV care products such as facial UV-protection emulsions, sun protection products, sun protectors, UV-care milk lotions, sunscreens, sunscreen creams, and suntan creams, gels such as moisturizing gels, facial peeling products, facial slimming products, and other basic care products.

Examples of the makeup products include base makeup products and point makeup products.

The base makeup products refer to basic makeup that is applied to complement point makeup, and refer to makeup base products, concealers, foundations, and face powders. Examples thereof include makeup base products such as makeup bases, base creams, color-controlling bases, and UV protection bases; concealers such as powdery concealers, cream concealers, and liquid concealers; foundations such as powdery foundations, UV protection foundations, cream foundations, and UV protection cream foundations; face powders such as loose powders, pressed powders, face color products, and white face powders.

The point makeup products refer to cosmetics for coloring the skin to make it look beautiful, and examples thereof include eye color products, eyeliners, eyelash liners, eyebrow cosmetics, blusher, lip color products, and nail color products.

Examples thereof include eye color products such as eye color powders, eye color pencils, and eye shadows; eyeliners such as eyeliner pencils and liquid eyeliners; eyelash liners such as volume-up eyelash liners, lone lash eyelash liners, curling eyelash liners, and color eyelash liners; eyebrow cosmetics such as eyebrow pencils, eyebrow powders, and liquid eyebrows; blusher such as powder blusher and cream blusher; lip color products such as lip color products, lipsticks, lip rouge, lip glosses, and lip liners; and nail color products such as nail color products, manicures, nail-top coats, base coats, top coats, over-top coats, nail color removers, nail polish removers, nail color thinners, and nail treatments.

Examples of the body cosmetics include body lotions, body creams, lip balms, hand creams, UV care products, depilatory products, foot care products, and antiperspirants/deodorants.

Examples thereof include body lotions such as body lotions, body oils, and body mists; body creams such as body creams, body milk lotions, body gels, and body mousses; lip balms such as moisturizing lip balms, UV-care lip balms, and colored lip balms; hand creams such as hand creams and hand gels; UV care products for body such as UV-protection emulsions, sun protection products, sun protectors, UV-care milk lotions, sunscreens, sunscreen creams, and suntan creams; depilatory products such as depilatory creams, depilatory mousses, depilatory waxes, body hair bleaches, and body shaving creams; foot care products such as foot massage products, foot slimming products, foot peeling products, non-facial exfoliators including exfoliators for heel, and emollient products; antiperspirants/deodorants such as deodorant lotions, deodorant powders, deodorant sprays, and deodorant sticks; and insect repellents such as insect repellent sprays.

Examples of the fragrance cosmetics include perfumes, parfums, eau de parfums, eau de toilettes, eau de colognes, solid perfumes, powder fragrances, perfumed soaps, and bath oils.

Examples of the hair care products include shampoos, hair rinses and conditioners, hair treatments and hair packs, hair styling products, hair sprays and hair glosses, hair growth promoters and pilatories, hair permanent products, and hair coloring products.

Examples thereof include shampoos such as oil shampoos, cream shampoos, conditioning shampoos, anti-dandruff shampoos, shampoos for colored hair, and 2-in-1 shampoos; hair rinses and conditioners such as hair rinses and conditioners, anti-dandruff/scalp-care hair rinses and conditioners, and control hair rinses and conditioners; hair treatments and packs such as damaged hair treatments and packs, damaged hair treatments and packs, anti-dandruff/scalp-care treatments and packs, and control treatments and packs; styling products such as hair foams, hair creams, hair wax, hair gels, hair water, hair lotions, hair oils, and hair liquids; hair sprays and hair glosses such as hair styling sprays, hair styling mists, and hair glosses, and hair growth promoters and pilatories such as hair growth promoters, pilatories, hair tonics, and hair essences; hair permanent products such as hair relaxers, wave permanent products, permanent pre-treatments, and permanent after-treatments; and hair coloring products such as oxidative hair dyes, hair bleaches, hair coloring pre-treatments, hair coloring after-treatments, and hair manicures.

The cosmetic produced by the production method of a cosmetic according to the present invention is in any cosmetic/dosage form. Preferred examples thereof include, but are not limited to, emulsions such as oil-in-water (O/W) emulsions, water-in-oil (W/O) emulsions, W/O/W emulsions, and O/W/O emulsions, oils, solids, liquids, pastes, sticks, volatile oils, powders, jellies, gels, pastes, emulsion polymers, sheets, mists, and sprays. The product takes any form and can be a cosmetic as a dispersion liquid, a milk lotion, a cream, a facial pack, a spray, a gel, a sheet, or the like.

EXAMPLES

The present invention will be described more specifically by Examples and Comparative Examples. The present invention is, however, not limited to the following Examples.

The meaning of abbreviations to be used in the following Examples and compounds used therein are as follows.
Gly: glycine
His: histidine
Carboxyvinyl polymer: Carbopol 940 (manufactured by ITO, Inc)
TEA: triethanolamine (manufactured by Junsei Chemical Co., Ltd.)
PG: propylene glycol
CMC: carboxymethylcellulose (manufactured by AS ONE Corporation)

In the tables below, "o" shows that a gel was formed, "x" shows that a gel was not folioed, and "–" shows that evaluation was not carried out.

In the present invention, even when syneresis (solvent separation) from a gel occurred, the gel can be used for production of a cosmetic.

Synthesis Example 1

Synthesis of N-Palmitoyl-Gly-His 14.2 g (91.6 mmol) of histidine, 30.0 g (91.6 mmol) of N-palmitoyl-Gly-methyl, and 300 g of toluene were put into a 500-mL four-necked flask, to which 35.3 g (183.2 mmol) of a 28% methanol solution of sodium methoxide as a base was added. The resultant solution was heated in an oil bath to 60° C. and was stirred for 1 hour. Subsequently, the resulting solution removed from the oil bath was left to cool to 25° C., reprecipitated with 600 g of acetone, and filtered off. The resulting solid was dissolved in a mixed solution of 600 g of water and 750 g of methanol, to which 30.5 ml, (183.2 mmol) of 6 N hydrochloric acid was added for neutralization to precipitate a solid, which was filtered off. The resulting solid was then dissolved in a mixed solution of 120 g of tetrahydrofuran and 30 g of water at 60° C., to which 150 g of ethyl acetate was added, and the resultant solution was cooled from 60° C. to 30° C. Subsequently, the precipitated solid was filtrated. The resulting solid was heated in a solvent of 120 g of tetrahydrofuran and 60 g of acetonitrile to 60° C., stirred for 1 hour, and then cooled, followed by filtration. The resulting solid was washed with 120 g of water and filtrated, followed by drying under reduced pressure to obtain 26.9 g (yield: 65%) of a white crystal of N-palmitoyl-Gly-His.

Example 1

Evaluation Test of Hydrogel-Forming Ability of Carboxyvinyl Polymer, TEA, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w) and the concentration of TEA was 0.015% by weight to 0.09% by weight (w/w). The resulting solution was then heated at 80° C. to 100° C. using a constant temperature heat block (manufactured by Nippon Genetics Co., Ltd.), and the transparent dispersion was visually observed. On the other hand, carboxyvinyl polymer was added in a screw tube (Maruemu No. 5, manufactured by Maruemu Corporation) so as to have a concentration of 0.025% by weight to 0.15% by weight (w/w) and heated to 80° C. using a constant temperature heat block (manufactured by Nippon Genetics Co., Ltd.). The TEA aqueous solution of N-palmitoyl-Gly-His in a heated dispersed state was added to the carboxyvinyl polymer in a heated state at a weight ratio of 1.1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 1 to Table 4.

TABLE 1

| Composition | Proportion (w/w %) | | | |
|---|---|---|---|---|
| N-palmitoyl-Gly-His | 0.2 | 0.25 | 0.5 | 1.0 |
| Carboxyvinyl polymer | 0.025 | 0.025 | 0.025 | 0.025 |
| TEA | 0.015 | 0.015 | 0.015 | 0.015 |
| Water | Balance | Balance | Balance | Balance |
| Total | 100 | 100 | 100 | 100 |
| Gel state | ○ | ○ | ○ | ○ |
| Syneresis | Observed | Observed | Observed | None |
| pH | 7.2 | 7.2 | 6.4 | 7.1 |

TABLE 2

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.05 | 0.05 | 0.05 | 0.05 | 0.05 |
| TEA | 0.03 | 0.03 | 0.03 | 0.03 | 0.03 |
| Water | Balance | Balance | Balance | Balance | Balance |
| Total | 100 | 100 | 100 | 100 | 100 |
| Gel state | ○ | ○ | ○ | ○ | ○ |
| Syneresis | None | None | None | None | None |
| pH | 7.2 | 6.5 | 6.7 | 6.5 | 6.6 |

TABLE 3

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.1 | 0.1 | 0.1 | 0.1 | 0.1 |
| TEA | 0.06 | 0.06 | 0.06 | 0.06 | 0.06 |
| Water | Balance | Balance | Balance | Balance | Balance |
| Total | 100 | 100 | 100 | 100 | 100 |
| Gel state | ○ | ○ | ○ | ○ | ○ |
| Syneresis | None | None | None | None | None |
| pH | 6.2 | 6.3 | 6.2 | 6.3 | 6.4 |

TABLE 4

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.15 | 0.15 | 0.15 | 0.15 | 0.15 |
| TEA | 0.09 | 0.09 | 0.09 | 0.09 | 0.09 |
| Water | Balance | Balance | Balance | Balance | Balance |
| Total | 100 | 100 | 100 | 100 | 100 |
| Gel state | ○ | ○ | ○ | ○ | ○ |
| Syneresis | None | None | None | None | None |
| pH | 5.9 | 5.5 | 5.9 | 5.9 | 5.9 |

Based on the results shown in Table 1 to Table 4, a gel was formed with a small use amount of the polymer thickener by blending the lipid peptide-type gelator at a certain ratio relative to the amount of carboxyvinyl polymer that is a polymer thickener.

Comparative Example 1

Evaluation Test of Hydrogel-Forming Ability of N-Palmitoyl-Gly-His, TEA

N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w) and the concentration of TEA was 0.015% by weight to 0.09% by weight (w/w). The resulting solution was then heated at 80° C. to 100° C. using a constant temperature heat block (manufactured by Nippon Genetics Co., Ltd.), and the transparent dispersion was visually observed. The solution was then left to cool at room temperature for one night. A state in which the fluidity of the solution was lost and the solution did not flow down when the screw tube was inverted was evaluated as "gelation(o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 5 to Table 8.

TABLE 5

| Composition | Proportion (w/w %) | | | |
|---|---|---|---|---|
| N-palmitoyl-Gly-His | 0.2 | 0.25 | 0.5 | 1.0 |
| TEA | 0.015 | 0.015 | 0.015 | 0.015 |
| Water | Balance | Balance | Balance | Balance |
| Total | 100 | 100 | 100 | 100 |
| Gel state | x | x | x | ○ |
| Syneresis | — | — | — | None |
| pH | 8.9 | 8.9 | 8.7 | 8.7 |

TABLE 6

| Composition | Proportion (w/w %) | | | | |
|---|---|---|---|---|---|
| N-palmitoyl-Gly-His | 0.1 | 0.2 | 0.25 | 0.5 | 1.0 |
| TEA | 0.03 | 0.03 | 0.03 | 0.03 | 0.03 |
| Water | Balance | Balance | Balance | Balance | Balance |
| Total | 100 | 100 | 100 | 100 | 100 |
| Gel state | x | x | x | x | ○ |
| Syneresis | — | — | — | — | Observed |
| pH | 9.0 | 8.9 | 9.0 | 8.8 | 8.8 |

TABLE 7

| Composition | Proportion (w/w %) | | | | |
|---|---|---|---|---|---|
| N-palmitoyl-Gly-His | 0.1 | 0.2 | 0.25 | 0.5 | 1.0 |
| TEA | 0.06 | 0.06 | 0.06 | 0.06 | 0.06 |
| Water | Balance | Balance | Balance | Balance | Balance |
| Total | 100 | 100 | 100 | 100 | 100 |
| Gel state | x | x | x | x | ○ |
| Syneresis | — | — | — | — | Observed |
| pH | 9.0 | 9.0 | 8.9 | 9.0 | 8.8 |

TABLE 8

| Composition | Proportion (w/w %) | | | | |
|---|---|---|---|---|---|
| N-palmitoyl-Gly-His | 0.1 | 0.2 | 0.25 | 0.5 | 1.0 |
| TEA | 0.09 | 0.09 | 0.09 | 0.09 | 0.09 |
| Water | Balance | Balance | Balance | Balance | Balance |
| Total | 100 | 100 | 100 | 100 | 100 |
| Gel state | x | x | x | x | ○ |
| Syneresis | — | — | — | — | Observed |
| pH | 9.2 | 9.2 | 9.2 | 9.1 | 9.1 |

Comparative Example 2

Evaluation Test of Hydrogel-Forming Ability of Carboxyvinyl Polymer, TEA

Carboxyvinyl polymer and TEA were added in a screw tube (Maruemu No. 5, manufactured by Maruemu Corporation) so that the concentration of carboxyvinyl polymer was 0.005% by weight to 0.25% by weight (w/w) and the concentration of TEA was 0.003% by weight to 0.15% by weight (w/w). The resulting solution was stirred with a vortex mixer (Scientific Industries Inc.) and left at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 9 and Table 10.

TABLE 9

| Composition | Proportion (w/w %) | | | |
|---|---|---|---|---|
| Carboxyvinyl polymer | 0.005 | 0.0125 | 0.025 | 0.05 |
| TEA | 0.003 | 0.0075 | 0.015 | 0.03 |
| Water | Balance | Balance | Balance | Balance |
| Total | 100 | 100 | 100 | 100 |
| Gel state | x | x | x | x |
| Syneresis | — | — | — | — |
| pH | | | | |

TABLE 10

| Composition | Proportion (w/w %) | | | |
|---|---|---|---|---|
| Carboxyvinyl polymer | 0.1 | 0.15 | 0.2 | 0.25 |
| TEA | 0.06 | 0.09 | 0.12 | 0.15 |
| Water | Balance | Balance | Balance | Balance |
| Total | 100 | 100 | 100 | 100 |
| Gel state | x | o | o | o |
| Syneresis | — | None | None | None |
| pH | | 6.0 | 5.9 | 5.8 |

Example 2

Evaluation Test of Hydrogel-Forming Ability of Carboxyvinyl Polymer, TEA, N-Palmitoyl-Gly-His with Solvents N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 0.5% by weight (w/w), the concentration of TEA was 0.015% by weight to 0.3by weight (w/w), and the concentration of each solvent was 5.0% by weight to 10.0% by weight (w/w). The resulting solution was then heated at 80° C. to 100° C. using a constant temperature heat block (manufactured by Nippon Genetics Co., Ltd.), and the transparent dispersion was visually observed. On the other hand, carboxyvinyl polymer was added in a screw tube (Maruemu No. 5, manufactured by Maruenut Corporation) so as to have a concentration of 0.025% by weight to 0.05% by weight (w/w) and heated at 80° C. using a constant temperature heat block (manufactured by Nippon Genetics Co., Ltd.). The aqueous solution of N-palmitoyl-Gly-His in a heated dispersed state was added to the carboxyvinyl polymer dispersion liquid in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 11 to Table 16.

TABLE 11

| Composition | Proportion (w/w %) | | |
|---|---|---|---|
| N-palmitoyl-Gly-His | 0.2 | 0.025 | 0.5 |
| Carboxyvinyl polymer | 0.025 | 0.025 | 0.025 |
| TEA | 0.015 | 0.015 | 0.015 |
| Glycerin | 5.0 | 5.0 | 5.0 |
| Water | Balance | Balance | Balance |
| Total | 100 | 100 | 100 |
| Gel state | o | o | o |
| Syneresis | Observed | None | None |
| pH | 7.1 | 7.0 | 7.1 |

TABLE 12

| Composition | Proportion (w/w %) | | | |
|---|---|---|---|---|
| N-palmitoyl-Gly-His | 0.1 | 0.2 | 0.25 | 0.5 |
| Carboxyvinyl polymer | 0.05 | 0.05 | 0.05 | 0.05 |
| TEA | 0.03 | 0.03 | 0.03 | 0.03 |
| Glycerin | 5.0 | 5.0 | 5.0 | 5.0 |
| Water | Balance | Balance | Balance | Balance |
| Total | 100 | 100 | 100 | 100 |
| Gel state | o | o | o | o |
| Syneresis | None | None | None | None |
| pH | 6.6 | 6.8 | 6.8 | 6.6 |

TABLE 13

| Composition | Proportion (w/w %) | | | |
|---|---|---|---|---|
| N-palmitoyl-Gly-His | 0.1 | 0.2 | 0.25 | 0.5 |
| Carboxyvinyl polymer | 0.025 | 0.025 | 0.025 | 0.025 |
| TEA | 0.015 | 0.015 | 0.015 | 0.015 |
| Glycerin | 10.0 | 10.0 | 10.0 | 10.0 |
| Water | Balance | Balance | Balance | Balance |
| Total | 100 | 100 | 100 | 100 |
| Gel state | o | o | o | o |
| Syneresis | Observed | Observed | None | None |
| pH | 6.8 | 6.8 | 6.8 | 7.1 |

TABLE 14

| Composition | Proportion (w/w %) | | | |
|---|---|---|---|---|
| N-palmitoyl-Gly-His | 0.1 | 0.2 | 0.25 | 0.5 |
| Carboxyvinyl polymer | 0.05 | 0.05 | 0.05 | 0.05 |

TABLE 14-continued

| Composition | Proportion (w/w %) | | | |
|---|---|---|---|---|
| TEA | 0.03 | 0.03 | 0.03 | 0.03 |
| Glycerin | 10.0 | 10.0 | 10.0 | 10.0 |
| Water | Balance | Balance | Balance | Balance |
| Total | 100 | 100 | 100 | 100 |
| Gel state | ○ | ○ | ○ | ○ |
| Syneresis | Observed | None | None | None |
| pH | 6.6 | 6.5 | 6.4 | 6.6 |

TABLE 15

| Composition | Proportion (w/w %) | | | |
|---|---|---|---|---|
| N-palmitoyl-Gly-His | 0.1 | 0.2 | 0.25 | 0.5 |
| Carboxyvinyl polymer | 0.025 | 0.025 | 0.025 | 0.025 |
| TEA | 0.015 | 0.015 | 0.015 | 0.015 |
| Propylene glycol | 5.0 | 5.0 | 5.0 | 5.0 |
| Water | Balance | Balance | Balance | Balance |
| Total | 100 | 100 | 100 | 100 |
| Gel state | ○ | ○ | ○ | ○ |
| Syneresis | None | None | None | None |
| pH | 6.6 | 7.3 | 7.3 | 7.3 |

TABLE 16

| Composition | Proportion (w/w %) | | | |
|---|---|---|---|---|
| N-palmitoyl-Gly-His | 0.1 | 0.2 | 0.25 | 0.5 |
| Carboxyvinyl polymer | 0.05 | 0.05 | 0.05 | 0.05 |
| TEA | 0.03 | 0.03 | 0.03 | 0.03 |
| Propylene glycol | 5.0 | 5.0 | 5.0 | 5.0 |
| Water | Balance | Balance | Balance | Balance |
| Total | 100 | 100 | 100 | 100 |
| Gel state | ○ | ○ | ○ | ○ |
| Syneresis | None | None | None | None |
| pH | 6.8 | 6.7 | 6.9 | 7.0 |

Based on the results in Table 1 to Table 4 and Table 11 to Table 16, according to the present invention, whether solvents were added or not did not make a difference in the effects of the invention.

Example 3

Evaluation Test of Hydrogel-Forming Ability of Gellan Gum, Citric Acid, Sodium Citrate Dihydrate, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w), the concentration of citric acid (manufactured by Wako Pure Chemical Industries, Ltd.) was 0.05% by weight (w/w), and the concentration of sodium citrate dihydrate (hereinafter also called Na citrate dihydrate) (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd.), and the transparent dispersion was visually observed. On the other hand, an aqueous solution of gellan gum (manufactured by KANTO CHEMICAL CO., INC.) having a concentration of 0.05% by weight to 0.25% by weight (w/w) was prepared in a screw tube (Maruemu No. 5, manufactured by Maruemu Corporation) and heated at 80° C. using as constant temperature heat block (manufactured by Nippon Genetics Co., Ltd.). The N-palmitoyl-Gly-His solution in a heated dispersed state was added to the gellan gum aqueous solution in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (○)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 17 to Table 20.

TABLE 17

| Composition | Proportion (w/w %) | | |
|---|---|---|---|
| N-palmitoyl-Gly-His | 0.25 | 0.5 | 1.0 |
| Gellan gum | 0.05 | 0.05 | 0.05 |
| Citric acid | 0.05 | 0.05 | 0.05 |
| Na citrate dihydrate | 0.62 | 0.62 | 0.62 |
| Water | Balance | Balance | Balance |
| Total | 100 | 100 | 100 |
| Gel state | ○ | ○ | x |
| Syneresis | Observed | None | — |
| pH | 6.1 | 6.2 | 6.1 |

TABLE 18

| Composition | Proportion (w/w %) | | | |
|---|---|---|---|---|
| N-palmitoyl-Gly-His | 0.1 | 0.25 | 0.5 | 1.0 |
| Gellan gum | 0.1 | 0.1 | 0.1 | 0.1 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | x | ○ | x |
| Syneresis | — | — | Observed | — |
| pH | 6.1 | 6.0 | 6.2 | 6.1 |

TABLE 19

| Composition | Proportion (w/w %) | | | |
|---|---|---|---|---|
| N-palmitoyl-Gly-His | 0.1 | 0.25 | 0.5 | 1.0 |
| Gellan gum | 0.2 | 0.2 | 0.2 | 0.2 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | ○ | ○ | ○ | ○ |
| Syneresis | Observed | Observed | Observed | Observed |
| pH | 6.0 | 6.2 | 6.0 | 6.1 |

TABLE 20

| Composition | Proportion (w/w %) | | | |
|---|---|---|---|---|
| N-palmitoyl-Gly-His | 0.1 | 0.25 | 0.5 | 1.0 |
| Gellan gum | 0.25 | 0.25 | 0.25 | 0.25 |

TABLE 20-continued

| Composition | Proportion (w/w %) | | | |
|---|---|---|---|---|
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | o | o | x |
| Syneresis | — | Observed | Observed | — |
| pH | 6.1 | 6.0 | 6.1 | 6.0 |

Based on the results in Table 17 to Table 20, a gel was formed with a small use amount of the polymer thickener by blending the lipid peptide-type gelator at a certain ratio relative to the amount of gellan gum that is a polymer thickener.

Comparative Example 3

Evaluation Test of Hydrogel-Forming Ability of Gellan Gum, Citric Acid, Sodium Citrate Dihydrate Gellan gum, citric acid, and sodium citrate dihydrate were added in a screw tube (Maruemu No. 5, manufactured by Maruemu Corporation) so that the concentration of gellan gum was 0.05% by weight to 0.25% by weight (w/w), the concentration of citric acid (manufactured by Wako Pure Chemical Industries, Ltd.) was 0.05% by weight (w/w), and the concentration of sodium citrate dihydrate (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd.), and the transparent dispersion was visually observed. The solution was then left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 21.

TABLE 21

| Composition | Proportion (w/w %) | | | |
|---|---|---|---|---|
| Gellan gum | 0.05 | 0.1 | 0.2 | 0.25 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | x | x | x |
| Syneresis | — | — | — | — |
| pH | 6.0 | 6.0 | 6.1 | 6.1 |

Example 4

Evaluation Test of Hydrogel-Forming Ability of Xanthan Gum, Citric Acid, Sodium Citrate Dihydrate, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w), the concentration of citric acid (manufactured by Wako Pure Chemical Industries, Ltd.) was 0.05% by weight (w/w), and the concentration of Na citrate dihydrate (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd.), and the transparent dispersion was visually observed. On the other hand, an aqueous solution of xanthan gum (manufactured by Tokyo Chemical Industry Co., Ltd.) having a concentration of 0.05% by weight to 0.25% by weight (w/w) was prepared in a screw tube (Maruemu No. 5, manufactured by Maruemu Corporation) and heated at 80° C. using a constant temperature heat block (manufactured by Nippon Genetics Co., Ltd.). The N-palmiloyl-Gly-His solution in a heated dispersed state was added to the xanthan gum aqueous solution in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 22 to Table 25.

TABLE 22

| Composition | Proportion (w/w %) | | |
|---|---|---|---|
| N-palmitoyl-Gly-His | 0.25 | 0.5 | 1.0 |
| Xanthan gum | 0.05 | 0.05 | 0.05 |
| Citric acid | 0.05 | 0.05 | 0.05 |
| Na citrate dihydrate | 0.62 | 0.62 | 0.62 |
| Water | Balance | Balance | Balance |
| Total | 100 | 100 | 100 |
| Gel state | o | o | o |
| Syneresis | Observed | Observed | None |
| pH | 6.1 | 6.1 | 6.1 |

TABLE 23

| Composition | Proportion (w/w %) | | | |
|---|---|---|---|---|
| N-palmitoyl-Gly-His | 0.1 | 0.25 | 0.5 | 1.0 |
| Xanthan gum | 0.1 | 0.1 | 0.1 | 0.1 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | o | o | o | o |
| Syneresis | Observed | Observed | Observed | None |
| pH | 6.2 | 6.1 | 6.1 | 6.1 |

TABLE 24

| Composition | Proportion (w/w %) | | | |
|---|---|---|---|---|
| N-palmitoyl-Gly-His | 0.1 | 0.25 | 0.5 | 1.0 |
| Xanthan gum | 0.2 | 0.2 | 0.2 | 0.2 |

TABLE 24-continued

| Composition | Proportion (w/w %) | | | |
|---|---|---|---|---|
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | ○ | ○ | ○ | ○ |
| Syneresis | Observed | None | None | None |
| pH | 6.0 | 6.2 | 6.2 | 6.2 |

TABLE 25

| Composition | Proportion (w/w %) | | | |
|---|---|---|---|---|
| N-palmitoyl-Gly-His | 0.1 | 0.25 | 0.5 | 1.0 |
| Xanthan gum | 0.25 | 0.25 | 0.25 | 0.25 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | ○ | ○ | ○ | ○ |
| Syneresis | Observed | None | None | None |
| pH | 6.2 | 6.1 | 6.1 | 6.1 |

Based on the results in Table 22 to Table 25, a gel was formed with a small use amount of the polymer thickener by blending the lipid peptide-type gelator at a certain ratio relative to the amount of xanthan gum that is a polymer thickener.

Comparative Example 4

Evaluation Test of Hydrogel-Forming Ability of Xanthan Gum, Citric Acid, Sodium Citrate Dihydrate Xanthan gum, citric acid, and sodium citrate dihydrate were added in a screw tube (Maruemu No. 5, manufactured by Maruemu Corporation) so that the concentration of xanthan gum was 0.05% by weight to 0.25% by weight (w/w), the concentration of citric acid (manufactured by Wako Pure Chemical industries, Ltd.) was 0.05% by weight (w/w), and the concentration of sodium citrate dihydrate (manufactured by KANTO CHEMICAL CO., INC,) was 0.62% by weight (w/w). The resulting solution was then heated at 80° C. to 100° C. using a constant temperature heat block (manufactured by Nippon Genetics Co., Ltd.), and the transparent dispersion was visually observed. The solution was then left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 26.

TABLE 26

| Composition | Proportion (w/w %) | | | |
|---|---|---|---|---|
| Xanthan gum | 0.05 | 0.1 | 0.2 | 0.25 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | x | x | x |
| Syneresis | — | — | — | — |
| pH | 6.1 | 6.1 | 6.1 | 6.1 |

Example 5

Evaluation Test of Hydrogel-Forming Ability of CMC, Citric Acid, Sodium Citrate Dihydrate, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w), the concentration of citric acid (manufactured by Wako Pure Chemical industries. Ltd.) was 0.05% by weight (w/w), and the concentration of sodium citrate dihydrate (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd), and the transparent dispersion was visually observed. On the other hand, an aqueous solution of CMC having a concentration of 0.05% by weight to 0.5% by weight (w/w) was prepared in a screw tube (Maruemu No. 5, manufactured by Maruemu Corporation) and heated at 80° C. using a constant temperature heat block (manufactured by Nippon Genetics Co., Ltd.). The N-palmitoyl-Gly-His solution in a heated dispersed state was added to the CMC aqueous solution in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent sepatation) in a gel occurred was also determined, and the pH of the sample that formed a gel was measured with a twin pH meter (manufactured by AS ONE Corporation). The final composition after the hydrogelation test and the obtained test results are shown in Table 27 to Table 31,

TABLE 27

| Composition | Proportion (w/w %) | | |
|---|---|---|---|
| N-palmitoyl-Gly-His | 0.25 | 0.5 | 1.0 |
| CMC | 0.05 | 0.05 | 0.05 |
| Citric acid | 0.05 | 0.05 | 0.05 |
| Na citrate dihydrate | 0.62 | 0.62 | 0.62 |
| Water | Balance | Balance | Balance |
| Total | 100 | 100 | 100 |
| Gel state | ○ | ○ | ○ |
| Syneresis | Observed | Observed | Observed |
| pH | 6.0 | 6.0 | 6.0 |

TABLE 28

| Composition | Proportion (w/w %) | | | |
|---|---|---|---|---|
| N-palmitoyl-Gly-His | 0.1 | 0.25 | 0.5 | 1.0 |
| CMC | 0.1 | 0.1 | 0.1 | 0.1 |

TABLE 28-continued

| Composition | Proportion (w/w %) | | | |
|---|---|---|---|---|
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | ○ | ○ | ○ |
| Syneresis | — | Observed | Observed | Observed |
| pH | 6.0 | 6.0 | 6.0 | 6.0 |

TABLE 29

| Composition | Proportion (w/w %) | | | |
|---|---|---|---|---|
| N-palmitoyl-Gly-His | 0.1 | 0.25 | 0.5 | 1.0 |
| CMC | 0.2 | 0.2 | 0.2 | 0.2 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | ○ | ○ | ○ |
| Syneresis | — | Observed | Observed | Observed |
| pH | 6.0 | 6.0 | 6.1 | 6.0 |

TABLE 30

| Composition | Proportion (w/w %) | | | |
|---|---|---|---|---|
| N-palmitoyl-Gly-His | 0.1 | 0.25 | 0.5 | 1.0 |
| CMC | 0.25 | 0.25 | 0.25 | 0.25 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | ○ | x | x |
| Syneresis | — | Observed | — | — |
| pH | 6.0 | 6.0 | 6.0 | 6.0 |

TABLE 31

| Composition | Proportion (w/w %) | | | |
|---|---|---|---|---|
| N-palmitoyl-Gly-His | 0.1 | 0.25 | 0.5 | 1.0 |
| CMC | 0.5 | 0.5 | 0.5 | 0.5 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | x | ○ | ○ | ○ |
| Syneresis | — | Observed | None | None |
| pH | 6.1 | 6.0 | 6.1 | 6.0 |

Based on the results in Table 27 to Table 31, a gel was formed with a small use amount of the polymer thickener by blending the lipid peptide-type gelator at a certain ratio relative to the amount of carboxymethylcellulose that is a polymer thickener.

Comparative Example 5

Evaluation Test of Hydrogel-Forming Ability of Citric Acid, Sodium Citrate Dihydrate, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmtoyl-Gly-His was 0.1% by weight to 1.0% by weight (w/w), the concentration of citric acid (manufactured by Wako Pure Chemical Industries, Ltd) was 0.05% by weight (w/w), and the concentration of sodium citrate dihydrate (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd.), and the transparent dispersion was visually observed. The solution was then left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 32.

TABLE 32

| Composition | Proportion (w/w %) | | | |
|---|---|---|---|---|
| N-palmitoyl-Gly-His | 0.1 | 0.25 | 0.5 | 1.0 |
| Citric acid | 0.05 | 0.05 | 0.05 | 0.05 |
| Na citrate dihydrate | 0.62 | 0.62 | 0.62 | 0.62 |
| Water | Balance | Balance | Balance | Balance |
| Total | 100 | 100 | 100 | 100 |
| Gel state | ○ | ○ | x | x |
| Syneresis | Observed | Observed | — | — |
| pH | 6.1 | 6.1 | 6.1 | 6.1 |

Comparative Example 6

Evaluation Test of Hydrogel-Forming Ability of CMC, Citric Acid, Sodium Citrate Dihydrate CMC, citric acid, and sodium citrate dihydrate were added in a screw tube (Maruemu No. 5, manufactured by Maruemu Corporation) so that the concentration of CMC was 0.05% by weight to 0.5% by weight (w/w), the concentration of citric acid (manufactured by Wako Pure Chemical Industries, Ltd.) was 0.05% by weight (w/w), and the concentration of sodium citrate dihydrate (manufactured by KANTO CHEMICAL CO., INC.) was 0.62% by weight (w/w). The resulting solution was then heated at 80° C. to 100° C. using a constant temperature heat block (manufactured by Nippon Genetics Co., Ltd.), and the transparent dispersion was visually observed. The solution was then left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that thnned a gel was measured with a twin pH meter (manufactured by AS ONE Corporation). The final composition after the hydrogelation test and the obtained test results are shown in Table 33.

TABLE 33

| Composition | Proportion (w/w %) | | | | |
|---|---|---|---|---|---|
| CMC | 0.05 | 0.1 | 0.2 | 0.25 | 0.5 |
| Citric acid | 0.05 | 0.05 | 0.05 | 0.05 | 0.05 |
| Na citrate dihydrate | 0.62 | 0.62 | 0.62 | 0.62 | 0.62 |
| Water | Balance | Balance | Balance | Balance | Balance |
| Total | 100 | 100 | 100 | 100 | 100 |
| Gel state | x | x | x | x | x |
| Syneresis | | | | | |
| pH | 6.0 | 6.0 | 6.1 | 6.1 | 6.1 |

Example 6

Evaluation Test of Hydrogel-Forming Ability of Carboxyvinyl Polymer, NaOH, N-Palmitoyl-Gly-His N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w) and the concentration of NaOH was 0.002% by weight to 0.016% by weight (w/w). The resulting solution was then heated at 80° C. to 100° C. using a constant temperature heat block (manufactured by Nippon Genetics Co., Ltd.), and the dispersion was visually observed. On the other hand, carboxyvinyl polymer was added in a screw tube (Maruemu No. 5, manufactured by Maruemu Corporation) so as to have a concentration of 0.025% by weight to 0.2% by weight (w/w) and heated at 80° C. using a constant temperature heat block (manufactured by Nippon Genetics Co., Ltd.). The NaOH aqueous solution of N-palmitoyl-Gly-His in a heated dispersed state was added to the carboxyyinyl polymer aqueous solution in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 34 to Table 37.

TABLE 34

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.025 | 0.025 | 0.025 | 0.025 | 0.025 |
| NaOH | 0.002 | 0.002 | 0.002 | 0.002 | 0.002 |
| Water | Balance | Balance | Balance | Balance | Balance |
| Total | 100 | 100 | 100 | 100 | 100 |
| Gel state | o | o | o | o | o |
| Syneresis | None | None | None | None | None |
| pH | 6.4 | 6.3 | 6.2 | 6.6 | 6.6 |

TABLE 35

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.05 | 0.05 | 0.05 | 0.05 | 0.05 |
| NaOH | 0.004 | 0.004 | 0.004 | 0.004 | 0.004 |
| Water | Balance | Balance | Balance | Balance | Balance |
| Total | 100 | 100 | 100 | 100 | 100 |
| Gel state | o | o | o | o | o |
| Syneresis | None | None | None | None | None |
| pH | 6.2 | 6.1 | 5.9 | 6.0 | 6.1 |

TABLE 36

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.1 | 0.1 | 0.1 | 0.1 | 0.1 |
| NaOH | 0.008 | 0.008 | 0.008 | 0.008 | 0.008 |
| Water | Balance | Balance | Balance | Balance | Balance |
| Total | 100 | 100 | 100 | 100 | 100 |
| Gel state | o | o | o | o | o |
| Syneresis | None | None | None | None | None |
| pH | 5.5 | 5.7 | 5.5 | 5.7 | 5.7 |

TABLE 37

| Composition | Proportion (w/w %) | | | | |
|---|---|---|---|---|---|
| N-palmitoyl-Gly-His | 0.1 | 0.2 | 0.25 | 0.5 | 1.0 |
| Carboxyvinyl polymer | 0.2 | 0.2 | 0.2 | 0.2 | 0.2 |
| NaOH | 0.016 | 0.016 | 0.016 | 0.016 | 0.016 |
| Water | Balance | Balance | Balance | Balance | Balance |
| Total | 100 | 100 | 100 | 100 | 100 |
| Gel state | o | o | o | o | o |
| Syneresis | None | None | None | None | None |
| pH | 4.8 | 5.0 | 5.0 | 5.5 | 5.3 |

Comparative Example 7

Evaluation Test of Hydrogel-Forming Ability of N-Palmitoyl-Gly-His, HaOH

N-palmitoyl-Gly-His synthesized in Synthesis Example 1 was added in a screw tube (Maruemu No. 5, manufactured by Maruemu Corporation) so that the concentration of N-palmitoyl-Gly-His was 0.1% by weight to 1.0% by weight (w/w) and the concentration of NaOH was 0.002% by weight to 0.016% by weight (w/w). The resulting solution was then heated at 80° C. to 100° C. using a constant temperature heat block (manufactured by Nippon Genetics Co., Ltd.), and the dispersion was visually observed. The solution was then left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 38 to Table 41.

TABLE 38

| Composition | Proportion (w/w %) | | | | |
|---|---|---|---|---|---|
| N-palmitoyl-Gly-His | 0.1 | 0.2 | 0.25 | 0.5 | 1.0 |
| NaOH | 0.002 | 0.002 | 0.002 | 0.002 | 0.002 |
| Water | Balance | Balance | Balance | Balance | Balance |
| Total | 100 | 100 | 100 | 100 | 100 |
| Gel state | x | x | x | x | o |
| Syneresis | — | — | — | — | Observed |
| pH | — | — | — | — | 9.0 |

TABLE 39

| Composition | Proportion (w/w %) | | | | |
|---|---|---|---|---|---|
| N-palmitoyl-Gly-His | 0.1 | 0.2 | 0.25 | 0.5 | 1.0 |
| NaOH | 0.004 | 0.004 | 0.004 | 0.004 | 0.004 |
| Water | Balance | Balance | Balance | Balance | Balance |
| Total | 100 | 100 | 100 | 100 | 100 |
| Gel state | x | x | x | x | x |
| Syneresis | — | — | — | — | — |
| pH | — | — | — | — | — |

TABLE 40

| Composition | Proportion (w/w %) | | | | |
|---|---|---|---|---|---|
| N-palmitoyl-Gly-His | 0.1 | 0.2 | 0.25 | 0.5 | 1.0 |
| NaOH | 0.008 | 0.008 | 0.008 | 0.008 | 0.008 |
| Water | Balance | Balance | Balance | Balance | Balance |
| Total | 100 | 100 | 100 | 100 | 100 |
| Gel state | x | x | x | x | x |
| Syneresis | — | — | — | — | — |
| pH | — | — | — | — | — |

TABLE 41

| Composition | Proportion (w/w %) | | | | |
|---|---|---|---|---|---|
| N-palmitoyl-Gly-His | 0.1 | 0.2 | 0.25 | 0.5 | 1.0 |
| NaOH | 0.016 | 0.016 | 0.016 | 0.016 | 0.016 |
| Water | Balance | Balance | Balance | Balance | Balance |
| Total | 100 | 100 | 100 | 100 | 100 |
| Gel state | x | x | x | x | x |
| Syneresis | — | — | — | — | — |
| pH | — | — | — | — | — |

Comparative Example 8

Evaluation Test of Hydrogel-Forming Ability of Carboxyvinyl Polymer, NaOH

Carboxyvinyl polymer and NaOH were added in a screw tube (Maruemu No. 5, manufactured by Maruemu Corporation) so that the concentration of carboxyvinyl polymer was 0.025% by weight to 0.2% by weight (w/w) and the concentration of NaOH was 0.002% by weight to 0.016% by weight (w/w). The resulting solution was stirred with a vortex mixer (Scientific Industries Inc.) and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 42.

TABLE 42

| Composition | Proportion (w/w %) | | | |
|---|---|---|---|---|
| Carboxyvinyl polymer | 0.025 | 0.05 | 0.1 | 0.2 |
| NaOH | 0.002 | 0.004 | 0.008 | 0.016 |
| Water | Balance | Balance | Balance | Balance |
| Total | 100 | 100 | 100 | 100 |
| Gel state | x | x | x | o |
| Syneresis | — | — | — | None |
| pH | — | — | — | 5.0 |

Example 7

Evaluation Test of Hydrogel-Forming Ability of Carboxyvinyl Polymer, N-Palmitoyl-Gly-His with Solvents N-palmitoyl-Gly-His synthesized in Synthesis Example 1 was added in a screw tube (Maruemu No. 5, manufactured by Maruemu Corporation) so that the concentration of N-palmitoyl-Gly-His was 0.25% by weight (w/w) and the concentration of each solvent is 10.0% by weight to 30.0% by weight (w/w). The resulting solution was then heated at 80° C. to 100° C. using a constant temperature heat block (manufactured by Nippon Genetics Co., Ltd.), and the dispersion was visually observed. On the other hand, as dispersion liquid was prepared in a screw tube (Maruemu No. 5, manufactured by Maruemu Corporation) so that the concentration of carboxyvinyl polymer was 0.025% by weight (w/w), and heated at 80° C. using a constant temperature heat block (manufactured by Nippon Genetics Co., Ltd.). The N-palmitoyl-Gly-His solution in a heated dispersed state was added to the carboxyvinyl polymer dispersion liquid in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 43.

TABLE 43

| Composition | Proportion (w/w %) | | |
|---|---|---|---|
| N-palmitoyl-Gly-His | 0.25 | 0.25 | 0.25 |
| Carboxyvinyl polymer | 0.025 | 0.025 | 0.025 |
| Glycerin | 20.0 | 30.0 | — |
| Propylene glycol | — | — | 10.0 |
| Water | Balance | Balance | Balance |
| Total | 100 | 100 | 100 |
| Gel state | o | o | o |
| Syneresis | None | None | None |
| pH | 6.0 | 5.9 | 6.4 |

Based on the results in Table 43, according to the present invention, even without addition of a neutralizer, a gel was formed and the effects of the invention were not impaired.

Comparative Example 9

Evaluation Test of Hydrogel-Forming Ability of Carboxyvinyl Polymer with Solvents Carboxyvinyl polymer and solvents were added in a screw tube (Maruemu No. 5, manufactured by Maruemu Corporation) so that the concentration of carboxyvinyl polymer was 0.025% by weight (w/w) and the concentration of each solvent was by weight to 30.0% by weight (w/w). The resulting solution was stirred with a vortex mixer (Scientific Industries Inc.) and left to cool at room temperature for one night. A state in which the fluidity of the solution was lost and the solution did not flow down when the screw tube was inverted was evaluated as "gelation (o)". Whether syneresis (solvent separation) in a gel occurred was also determined, and the pH of the sample that formed a gel was measured with a twin pH meter (manufactured by AS ONE Corporation). The final composition after the hydrogelation test and the obtained test results are shown in Table 44.

TABLE 44

| Composition | Proportion (w/w %) | | |
|---|---|---|---|
| Carboxyvinyl polymer | 0.025 | 0.025 | 0.025 |
| Glycerin | 20.0 | 30.0 | — |
| Propylene glycol | — | — | 10.0 |
| Water | Balance | Balance | Balance |
| Total | 100 | 100 | 100 |
| Gel state | x | x | x |
| Syneresis | — | — | — |
| pH | 4.9 | 4.9 | 5.1 |

Example 8

Hydrogel Spray Test of Carboxyvinyl Polymer, TEA, N-palmitoyl-Gly-His

N-palmitoyl-Gly-His synthesized in Synthesis Example 1 was added in a screw tube (Marnemu No. 5, manufactured by Maruemu Corporation) so that the concentration of N-palmitoyl-Gly-His was 0.2% by weight (w/w %), the concentration of TEA was 0.015% by weight (w/w %), and the concentration of each solvent was 5.0% by weight (w/w %). The resulting solution was then heated at 80° C. to 100° C. using a constant temperature heat block (manufactured by Nippon Genetics Co., Ltd.), and the transparent dispersion was visually observed. On the other hand, carboxyvinyl polymer was added in a spray vial (3 L, manufactured by Maruemu Corporation) so as to have a concentration of 0.025% by weight (w/w %) and heated at 80° C. using a constant temperature heat block (manufactured by Nippon Genetics Co., Ltd.). The N-palmitoyl-Gly-His solution in a heated dispersed state was added to the carboxyvinyl polymer dispersion liquid in a heated state at a weight ratio of 1:1, stirred with a vortex mixer (Scientific Industries Inc.), and left to cool at room temperature for one night. A state in which the fluidity of the solution was lost and the solution did not flow down when the screw tube was inverted was evaluated as "gelation (o)".

The gel was sprayed from the spray vial (3 L, manufactured by Maruemu Corporation) containing the gel, successively twice toward the center of a glass plate (5 cm×5 cm at a distance of 5 cm from the nozzle tip of the spray vial. After observation for 1 minute, the longer diameter, the shorter diameter, and the length of dripping of the sprayed product on the glass were measured. The final composition after the hydrogelation test and the spray test results are shown in Table 45.

TABLE 45

| Composition | Proportion (w/w %) | | |
|---|---|---|---|
| N-palmitoyl-Gly-His | 0.2 | 0.2 | 0.2 |
| Carboxyvinyl polymer | 0.025 | 0.025 | 0.025 |
| TEA | 0.015 | 0.015 | 0.015 |
| Glycerin | — | 5.0 | — |
| Propylene glycol | — | — | 5.0 |
| Water | Balance | Balance | Balance |
| Total | 100 | 100 | 100 |
| Gel state | o | o | o |
| Spray length (mm) | 19 | 22 | 18 |
| Spray width (mm) | 22 | 19 | 19 |
| Dripping | None | None | None |

Basically, carboxyvinyl polymer as a polymer thickener cannot be used in the form of spray. The present invention, however, can reduce the use amount of carboxyvinyl polymer by blending N-palmitoyl-Gly-His at a certain ratio relative to the amount of carboxyvinyl polymer, which enables the use of carboxyvinyl polymer in the form of spray. Based on the results shown in Table 45, the present invention can significantly reduce the use amount of the polymer thickener, which can improve dripping of the cosmetic due to inclusion of the polymer thickener.

[Evaluation of Feel in Use]

A gel for cosmetics was prepared according to Example 9 and Comparative Example 10 below, and stretching on the skin surface, permeation into the skin, stickiness, and crinkles were evaluated based on the following evaluation criteria. Evaluation results are shown in Table 48.

<Evaluation Criterion for Stretching on Skin Surface>

When a cosmetic was applied on the skin, a sample that was stretched on the skin surface smoothly without roughness was evaluated as o, while a sample that stretched smoothly or with roughness was evaluated as x.

<Evaluation Criterion for Permeation into Skin>

When a cosmetic was applied on the skin, a sample that rapidly permeated into the skin and was absorbed into the skin to moisturize it was evaluated as o, while a sample that was not absorbed into the skin to moisturize it was evaluated as x.

<Evaluation Criterion for Stickiness>

After a cosmetic was applied on the skin, a sample that caused no stickiness lingering on the skin surface was evaluated as o, while a sample that caused stickiness lingering on the skin surface was evaluated as x.

<Evaluation Criterion for Crinkles>

After a cosmetic was applied on the skin and dried, a sample that caused no crinkles was evaluated as o, while a sample that caused crinkles was evaluated as x.

[Example 9: Feel in Use of Hydrogel-Like Cosmetic Containing Carboxyvinyl Polymer, TEA, and N-Palmitoyl-Gly-His]

N-palmitoyl-Gly-His synthesized in Synthesis Example 1 was added in a screw tube (Maruemu No. 5, manufactured by Maruemu Corporation) so that the concentration of N-palmitoyl-Gly-His was 0.2% by weight (w/w) and the concentration of TEA was 0.03% by weight (w/w). The resulting solution was then heated at 80° C. using a constant temperature heat block (manufactured by Nippon Genetics Co., Ltd), and the transparent dispersion was visually observed. On the other hand, carboxyvinyl polymer was added in a screw tube (Maruemu No. 5, manufactured by Maruemu Corporation) so as to have a concentration of 0.05% by weight (w/w) and heated to 80° C. using a constant temperature heat block (manufactured by Nippon Genetics Co., Ltd.). The TEA aqueous solution of N-palmitoyl-Gly-His in a heated dispersed state was added to the carboxyvinyl polymer in a heated state at a weight ratio of 1:1, stirred with a vortex mixer (Scientific Industries Inc.), and left to cool at room temperature, resulting in a state (gel) in which the fluidity of the solution was lost and the solution did not flow down when the screw tube was inverted. The composition of the resulting gel-like cosmetic is shown in Table 46, and the evaluation results of the feel in use are shown in Table 48.

TABLE 46

Composition of a hydrogel-like cosmetic containing carboxyvinyl polymer, TEA, and N-palmitoyl-Gly-His

| Composition | Proportion (w/w %) |
| --- | --- |
| N-palmitoyl-Gly-His | 0.2 |
| Carboxyvinyl polymer | 0.05 |
| TEA | 0.03 |
| Water | Balance |
| Total | 100 |

Comparative Example 10

Feel in Use of Hydrogel-Like Cosmetic Containing Carboxyvinyl Polymer and TEA

Carboxyvinyl polymer and TEA were added in a screw tube (Maruemu No. 5, manufactured by Maruemu Corporation) so that the concentration of carboxyvinyl polymer was 0.2% by weight (w/w) and the concentration of TEA was 0.12% by weight (w/w). The resulting solution was stirred with a vortex mixer (Scientific Industries Inc.) and left at room temperature for one night, resulting in a state (gel) in which the fluidity of the solution was lost and the solution did not flow down when the screw tube was inverted. The composition of the resulting gel-like cosmetic is shown in Table 47, and the evaluation results of the feel in use are shown in Table 48.

TABLE 47

Composition of a hydrogel-like cosmetic containing carboxyvinyl polymer and TEA

| Composition | Proportion (w/w %) |
| --- | --- |
| Carboxyvinyl polymer | 0.2 |
| TEA | 0.12 |
| Water | Balance |
| Total | 100 |

TABLE 48

Evaluation results of feel in use of Example 9 and Comparative Example 10

| | Example 9 | Comparative Example 10 |
| --- | --- | --- |
| Stretching on skin surface | ○ | ○ |
| Permeation into skin | ○ | ○ |
| Stickiness | ○ | x |
| Crinkles | ○ | x |

Based on the results of Example 9 and Comparative Example 10 in Table 48, the cosmetic gel prepared by the preparation method of a gel for cosmetics according to the present Invention produced a good result without stickiness or crinkles in spite of the blending of carboxyvinyl polymer.

The invention claimed is:

1. A production method of a cosmetic for producing a cosmetic in which a polymer thickener is blended in a cosmetic raw material, comprising: blending, into the cosmetic raw material in addition to the polymer thickener, at least one lipid peptide gelator that contains a low-molecular weight lipid peptide or a pharmaceutically usable salt of the low-molecular weight lipid peptide at a concentration of 0.1% by weight to 0.5% by weight based on a total mass of the cosmetic raw material to form a thickening gel, wherein the low-molecular weight lipid peptide is of Formula (1):

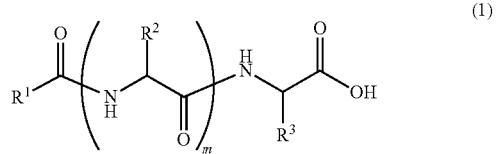

where $R^1$ is a $C_{9-23}$ aliphatic group; $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH^2)$n-X group; at least one of $R^2$ and $R^3$ is a —$(CH_2)$n-X group; n is 1 to 4; X is an amino group, a guanidino group, a carbarnoyl group, a 5-membered ring group optionally containing 1 to 3 nitrogen atoms, a 6-membered ring group optionally containing 1 to 3 nitrogen atoms, or a condensed ring group that contains a 5-membered ring and a 6-membered ring optionally containing 1 to 3 nitrogen atoms; and m is 1 to 3.

2. The production method of a cosmetic according to claim 1, wherein the polymer thickener is carboxyvinyl polymer, carboxymethylcellulose, gellan gum, or xanthan gum.

3. The production method of a cosmetic according to claim 2, wherein relative to a total mass of the cosmetic raw material, when the polymer thickener is carboxyvinyl polymer, a concentration of the carboxyvinyl polymer is 0.025% by weight to 0.05% by weight, when the polymer thickener is carboxymethylcellulose, a concentration of the carboxymethylcellulose is 0.05% by weight to 0.1% by weight, when the polymer thickener is gellan gum, a concentration of the gellan gum is 0.05% by weight to 0.1% by weight, and when the polymer thickener is xanthan gum, a concentration of the xanthan gum is 0.05% by weight to 0.1% by weight.

4. The production method of a cosmetic according to claim 1, wherein a molecular weight of the low-molecular weight lipid peptide is 1,000 or less.

5. The production method of a cosmetic according to claim 1, wherein in Formula (1), $R^2$ is a hydrogen atom, a methyl group, an isopropyl group, an isobutyl group, or a sec-butyl group.

6. The production method of a cosmetic according to claim 1, wherein in Formula (1), $R^3$ is a 4-aminobutyl group, a 4-imidazole methyl group, a carbamoylmethyl group, a carbamoylethyl group, or a 3-methylindole group.

7. The production method of a cosmetic according to claim 1, wherein in Formula (1), $R^1$ is a $C_{13-17}$ aliphatic group, $R^2$ is a hydrogen atom, a methyl group, or an isopropyl group, and $R^3$ is a 4-aminobutyl group, a 4-imidazole methyl group, or a 3-methylindole group.

8. The production method of a cosmetic according to claim 7, wherein in Formula (1), $R^2$ is a hydrogen atom and $R^3$ is a 4-imidazole methyl group.

9. A preparation method of a gel for cosmetics for preparing a thickening gel for cosmetics, comprising: blending, into an aqueous medium for cosmetics, a polymer thickener and at least one lipid peptide gelator that contains a low-molecular weight lipid peptide or a pharmaceutically usable salt of the low-molecular weight lipid peptide at a concentration of 0.1% by weight to 0.5% by weight based on a total mass of the thickening gel to form a gel,
wherein the low-molecular weight lipid peptide is of Formula (1):

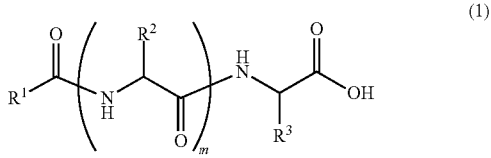

(1)

where $R^1$ is a $C_{9-23}$ aliphatic group; $R^2$ and $R^3$ are independently a hydrogen atom, a methyl group, an ethyl group, a $C_{3-7}$ alkyl group that optionally contains a $C_{1-3}$ branched chain, a phenylmethyl group, a phenylethyl group, or a —$(CH_2)n$-X group; at least one of $R^2$ and $R^3$ is a —$(CH_2)n$-X group; n is 1 to 4 X is an amino group, a guanidino group, a carbamoyl group, a 5-membered ring group optionally containing 1 to 3 nitrogen atoms, a 6-membered ring group optionally containing 1 to 3 nitrogen atoms, or a condensed ring group that contains a 5-membered ring and a 6-memebered ring optionally containing and 1 to 3 nitrogen atoms; and m is 1 to 3.

10. The preparation method of a gel for cosmetics according to claim 9, wherein the polymer thickener is carboxyvinyl polymer, carboxymethylcellulose, gellan gum, or xanthan gum.

11. The preparation method of a gel for cosmetics according to claim 10, wherein relative to a concentration of the thickening gel, when the polymer thickener is carboxyvinyl polymer, a concentration of the carboxyvinyl polymer is 0.025% by weight to 0.05% by weight, when the polymer thickener is carboxymethylcellulose, a concentration of the carboxymethylcellulose is 0.05% by weight to 0.1% by weight, when the polymer thickener is gellan gum, a concentration of the gellan gum is 0.05% by weight to 0.1% by weight, and when the polymer thickener is xanthan gum, a concentration of the xanthan gum is 0.05% by weight to 0.1% by weight.

12. The preparation method of a gel for cosmetics according to claim 9, wherein a molecular weight of the low-molecular weight lipid peptide is 1,000 or less.

13. The preparation method of a gel for cosmetics according to claim 9, wherein in Formula (1), $R^2$ is a hydrogen atom, a methyl group, an isopropyl group, an isobutyl group, or a sec-butyl group.

14. The preparation method of a gel for cosmetics according to claim 9, wherein in Formula (1), $R^3$ is a 4-aminobutyl group, a 4-imidazole methyl group, a carbamoylmethyl group, a carbamoylethyl group, or a 3-methylindole group.

15. The preparation method of a gel for cosmetics according to claim 9, wherein in Formula (1), $R^1$ is a $C_{13-17}$ aliphatic group, $R^2$ is a hydrogen atom, a methyl group, or an isopropyl group, and $R^3$ is a 4-aminobutyl group, a 4-imidazole methyl group, or a 3-methylindole group.

16. The preparation method of a gel for cosmetics according to claim 15, wherein in Formula (1), $R^2$ is a hydrogen atom and $R^3$ is a 4-imidazole methyl group.

17. A method of reducing the use amount of a polymer thickener in production of a cosmetic as claimed in claim 1 in which a polymer thickener is blended in a cosmetic raw material, comprising: blending, into the cosmetic raw material in addition to the polymer thickener, at least one lipid peptide gelator that contains a low-molecular weight lipid peptide or a pharmaceutically usable salt of the low-molecular weight lipid peptide at a ratio of 0.1% by weight to 0.5% by weight based on a mass of the cosmetic raw material.

* * * * *